United States Patent
Reisman et al.

(10) Patent No.: US 11,481,897 B2
(45) Date of Patent: Oct. 25, 2022

(54) OCT ANGIOGRAPHY CALCULATION WITH OPTIMIZED SIGNAL PROCESSING

(71) Applicant: Kabushiki Kaisha TOPCON, Tokyo (JP)

(72) Inventors: Charles A. Reisman, Mamaroneck, NY (US); Zhenguo Wang, Ridgewood, NJ (US); Atsushi Kubota, Tokyo (JP); Jonathan Liu, New York, NY (US)

(73) Assignee: Kabushiki Kaisha TOPCON, Tokyo (JP)

( * ) Notice: Subject to any disclaimer, the term of this patent is extended or adjusted under 35 U.S.C. 154(b) by 168 days.

(21) Appl. No.: 16/930,715

(22) Filed: Jul. 16, 2020

(65) Prior Publication Data
US 2020/0349701 A1    Nov. 5, 2020

Related U.S. Application Data

(63) Continuation of application No. 15/964,871, filed on Apr. 27, 2018, now Pat. No. 10,719,933, which is a (Continued)

(51) Int. Cl.
*G06T 7/00* (2017.01)
*G06T 5/50* (2006.01)
(Continued)

(52) U.S. Cl.
CPC .......... *G06T 7/0012* (2013.01); *A61B 5/0035* (2013.01); *A61B 5/0066* (2013.01);
(Continued)

(58) Field of Classification Search
CPC . A61B 5/02007; A61B 5/0035; A61B 5/0066; A61B 5/7257; A61B 5/7425;
(Continued)

(56) References Cited

U.S. PATENT DOCUMENTS 6,293,674 B1   9/2001   Huang et al.
7,148,970 B2  12/2006   de Boer
(Continued)

OTHER PUBLICATIONS

Tokayer et al. "Blood flow velocity quantification using split-spectrum amplitude-decorrelation angiography with optical coherence tomography." Biomedical optics express 4.10 (2013): 1909-1924. (Year: 2013).*
(Continued)

*Primary Examiner* — Katrina R Fujita
(74) *Attorney, Agent, or Firm* — Pearne & Gordon LLP

(57) ABSTRACT

Methods and systems for angiographic imaging with optical coherence tomography (OCT) are described using ratio-based and angiographic deviation based calculations. In using these calculations to determine motion, arbitrary inter-frame permutations may be used, post- calculated, non-linear results for projection visualization may be averaged, poor matches may be eliminated on an A-line by A-line basis, windowing functions may be used to improve results, partial spectrums may be used when capturing data, and a minimum intensity threshold may be used for determining which pixels to use.

16 Claims, 10 Drawing Sheets

Related U.S. Application Data continuation of application No. 15/091,288, filed on Apr. 5, 2016, now Pat. No. 9,984,459.

(60) Provisional application No. 62/147,911, filed on Apr. 15, 2015, provisional application No. 62/171,533, filed on Jun. 5, 2015, provisional application No. 62/222,767, filed on Sep. 23, 2015, provisional application No. 62/263,389, filed on Dec. 4, 2015.

(51) Int. Cl.
  *G06V 10/42* (2022.01)
  *A61B 5/00* (2006.01)
  *A61B 5/02* (2006.01)
  *G06K 9/62* (2022.01)

(52) U.S. Cl.
  CPC ........ *A61B 5/02007* (2013.01); *A61B 5/7257* (2013.01); *A61B 5/7425* (2013.01); *G06K 9/6215* (2013.01); *G06T 5/50* (2013.01); *G06V 10/42* (2022.01); *G06T 2207/10101* (2013.01); *G06T 2207/20052* (2013.01); *G06T 2207/20212* (2013.01); *G06T 2207/30041* (2013.01); *G06T 2207/30101* (2013.01); *G06T 2207/30104* (2013.01)

(58) Field of Classification Search
  CPC ....... G06K 9/6215; G06T 5/50; G06T 7/0012; G06T 2207/10101; G06T 2207/20052; G06T 2207/30041; G06T 2207/30101; G06T 2207/30104; G06V 10/42
  See application file for complete search history.

(56) References Cited

U.S. PATENT DOCUMENTS

| | | | |
|---|---|---|---|
| 7,301,644 | B2 | 11/2007 | Knighton et al. |
| 7,982,879 | B2 | 7/2011 | Desjardins et al. |
| 3,016,419 | A1 | 9/2011 | Zhang et al. |
| 8,687,666 | B2 | 4/2014 | Goldberg et al. |
| 9,596,993 | B2 | 3/2017 | Kemp et al. |
| 9,677,869 | B2 | 6/2017 | Berkeley et al. |
| 9,700,199 | B2 | 7/2017 | Tomatsu et al. |
| 9,763,569 | B2 | 9/2017 | Fingler et al. |
| 9,848,769 | B2 | 12/2017 | Miyasa et al. |
| 9,872,614 | B2 | 1/2018 | Nakano |
| 2006/0055936 | A1 | 3/2006 | Yun et al. |
| 2007/0038040 | A1 | 2/2007 | Cense et al. |
| 2007/0216908 | A1 | 9/2007 | Li et al. |
| 2007/0263227 | A1 | 11/2007 | Mujat et al. |
| 2007/0276269 | A1 | 11/2007 | Yun et al. |
| 2009/0268159 | A1 | 10/2009 | Xu et al. |
| 2012/0213423 | A1 | 8/2012 | Xu et al. |
| 2012/0288175 | A1 | 11/2012 | Iwase et al. |
| 2012/0307014 | A1 | 12/2012 | Wang |
| 2013/0301008 | A1 | 11/2013 | Srivastava et al. |
| 2014/0073917 | A1 | 3/2014 | Huang et al. |
| 2014/0218686 | A1 | 8/2014 | Reisman |
| 2014/0221827 | A1 | 8/2014 | Motaghiannezam et al. |
| 2015/0092195 | A1 | 4/2015 | Blatter et al. |
| 2016/0106310 | A1 | 4/2016 | Moriguchi |

OTHER PUBLICATIONS

Moult et al. "Ultrahigh-speed swept-source OCT angiography in exudative AMD." Ophthalmic Surgery, Lasers and Imaging Retina 45.6 (2014): 496-505. (Year: 2014).*

Blatter, et al., "Ultrahigh-speed non-invasive widefield angiograph", Journal of biomedical optics. vol. 17, No. 7, (2012): 0705051-0705053.

Braaf, et al., "Real-time eye motion correction in phase-resolved OCT angiography with tracking SLO," Biomed. Opt. Express 4(1), 51-65 (2013).

Chan, et al., "Quantitative Morphometry of Perifoveal Capillary Networks in the Human Retina," Invest. Ophthalmol. Vis. Sci. 53(9), pp. 5502-5514 (2012).

Drexler, et al., "Optical coherence tomography today: speed, contrast, and multimodality" IN: Journal of Biomedical Optics, Jul. 2014, vol. 19 (7), pp. 071412-1-071412-34.

Fercher, "Optical Coherence tomography—development, principles, applications." Zeitschrift fur Medizinische Physik 20.4 (2009): pp. 251-276.

Fercher, et al. , "Optical coherence tomography-principles and applications." Reports on progress in physics 66.2 (2003): 239.

Fingler, et al., "Mobility and Transverse Flow Visualization Using Phase Variance Contrast With Spectral Domain Optical Coherence Tomography" Optics Express, Oct. 1, 2007, vol. 15, No. 20, pp. 12636-12653.

Harris, "On the Use of Windows for Harmonic Analysis Awith the Discrete Fourier Fransfrom" Proceedings of the IEEE, Jan. 1, 1978, vol. 66, No. 1, pp. 51-83.

Hendargo, et al., "Automated non-rigid registration and mosaicing for robust imaging of distinct retinal capillary beds using speckle variance optical coherence tomography," Biomed. Opt. Express 4(6), pp. 803-821 (2013).

Huang, et al., "Efficient method to suppress artifacts caused by tissue hyper-reflections in optical microangiography of retina in vivo," Biomed. Opt. Express 6(4), 1195-1208 (2015).

Huang, et al., "Optical coherence tomography angiography of time course of choroidal neovascularization in response to anti-angiogenic treatment," Retina 35(11), pp. 2260-2264 (2015).

Hwang, et al., "Optical oherence Tomography Angiography Features of Diabetic Retinopathy," Retina 35(11), 2371-2376 (2015).

Jia, et al., "Quantitative OCT angiography of optic nerve head blood flow." Biomedical optics express 3.12 (2012): 3127-3137.

Jia, et al., "Quantitative optical coherence tomography angiography of vascular abnormalities in the living human eye," Proc. Natl. Acad. Sci. U.S.A. 112(18), E2395-E2402 (2015).

Jia, et al., "Quantitative optical coherence tomography angiography of choroidal neovascularization in age-related macular degeneration," Ophthalmology 121(7), 1435-1444 (2014).

Jia, et al., "Split-spectrum amplitude-decorrelation angiography with optical coherence tomography," Opt. Express 20(4), 4710-4725 (2012).

Kurokawa, et al., "Three-dimensional retinal and choroidal capillary imaging by power Doppler optical coherence angiography with adaptive optics," Opt. Express 20(20), 22796-22812 (2012).

Liu, et al., "Automated choroidal neovascularization detection algorithm for optical coherence tomography angiography," Biomed. Opt. Express 6(9), pp. 3564-3576 (2015).

Mahmud, et al., "Review of speckle and phase variance optical coherence tomography to visualize microvascular networks." Journal of Biomedical Optics, vol. 18, No. 5, May 2013, pp. 050901-1-050901-13.

Makita, et al., "Comprehensive in vivo micro-vascular imaging of the human eye by dual-beam-scan Doppler optical coherence angiography," Opt. Express 19(2), 1271-1283 (2011).

Makita, et al., "Optical Coherence Angiography" Optics Express, Aug. 21, 2006, vol. 14, No. 17 pp. 7821-7840.

Mariampillai, et al., "Speckle Variance Detection of Microvasculature Using Swept-Source Optical Coherence Tomography" Optics Letters, Jul. 1, 2008, vol. 33, No. 13, pp. 1530-1532.

Michaely, et aL., "Vectorial reconstruction of retinal blood flow in three dimensions measured with high resolution resonant Doppler Fourier domain optical coherence tomography." Journal of Biomedical Optics, vol. 12, No. 4, Jul./Aug. 2007, pp. 041213-1-041213-7.

Palejwala, et al., "Detection of non-exudative choroidal neovascularization in age-related macular degeneration with optical coherence tomography angiography," Retina 35(11), pp. 2204-2211 (2015).

Podoleanu, et al., "Combinations of techniques in imaging the retina with high resolution" IN: Progress in Retinal Eye Research 27 (2008), pp. 464-499.

(56) References Cited

OTHER PUBLICATIONS

Schmitt, "Optical coherence tomography (OCT): a review." IEEE Journal of selected topics in quantum electronics, vol. 5, No. 4, Jul./Aug. 1999, pp. 1205-1215.
Spaide, et al., "Image artifacts in optical coherence tomography angiography," Retina 35(11), pp. 2163-2180 (2015).
Extended European Search Report for 16165027.0 dated Sep. 23, 2016.
Wang, et al., "Three dimensional optical angiography", Optics Express, vol. 15, No. 7, Apr. 7, 2007, pp. 1083-4097.
Zhang, et al., "Advanced image processing for optical coherence tomographic angiography of macular diseases," Biomed. Opt. Express 6(12), pp. 4661-4675 (2015).
Zhang, et al., "Methods and algorithms for optical coherence tomography-based angiography: a review and comparison", Journal of Biomedical Optics , vol. 20, No. 10, Oct. 2015, pp. 100901-1-100901-13.
Zhang, et al., "Minimizing projection artifacts for accurate presentation of choroidal neovascularization in OCT micro-angiography," Biomed. Opt. Express 6(10), pp. 4130-4143 (2015).
Liu, et al., "Optimized doppler optical coherence tomography for choroidal capillary vasculature imaging", Optical Coherence Tomography and Coherence Domain Optical Methods in Biomedicine XV. vol. 7889, International Society for Optics and Photonics, (2011).

\* cited by examiner

SSADA-based Implementation

Ratio-Based Implementation

**Standard Deviation
Interframe Implementation**

**Ratio-Based
Implementation**

OCT ANGIOGRAPHY CALCULATION WITH OPTIMIZED SIGNAL PROCESSING

CROSS REFERENCE TO RELATED APPLICATIONS

This application claims priority to U.S. application Ser. No. 15/964,871, filed on Apr. 27, 2018, entitled "OCT ANGIOGRAPHY CALCULATION WITH OPTIMIZED SIGNAL PROCESSING", which claims priority to U.S. application Ser. No. 15/091,288, filed on Apr. 5, 2016, entitled "OCT ANGIOGRAPHY CALCULATION WITH OPTIMIZED SIGNAL PROCESSING", which issued as U.S. Pat. No. 9,984,459 on May 29, 2018, and which claims priority to: (1) U.S. Provisional Application Ser. No. 62/147,911, filed on Apr. 15, 2015, entitled "OCT ANGIOGRAPHY USING A RATIO-BASED CALCULATION WITH OPTIMIZED SIGNAL PROCESSING"; (2) U.S. Provisional Application Ser. No. 62/171,533, filed on Jun. 5, 2015, entitled "OCT ANGIOGRAPHY USING A RATIO-BASED CALCULATION WITH OPTIMIZED SIGNAL PROCESSING"; (3) U.S. Provisional Application Ser. No. 62/222,767, filed on Sep. 23, 2015, entitled "OCT ANGIOGRAPHY USING A RATIO-BASED CALCULATION WITH OPTIMIZED SIGNAL PROCESSING"; and (4) U.S. Provisional Application Ser. No. 62/263,389, filed on Dec. 4, 2015, entitled "OCT ANGIOGRAPHY USING A RATIO-BASED CALCULATION WITH OPTIMIZED SIGNAL PROCESSING", the entireties of which are incorporated herein by reference.

BACKGROUND OF THE INVENTION

1. Field of the Invention

This application relates generally to optical coherence tomography (OCT), and more specifically, to angiographic OCT.

2. Description of Related Art

Angiographic optical coherence tomography (OCT) is a technique that visualizes vasculature based on three dimensional (3D) OCT volume information. The underlying concept of OCT angiography is that the blood flow inside vasculature induces motion that manifests as changes in relative phase and/or pixel intensity in OCT imaging over time. OCT angiography processes visualize such phase and/or intensity changes to represent vasculature. Such changes are assumed to originate from blood flow and are, therefore, assumed to represent vasculature. 3D OCT can be used for angiographic purposes, as it possesses sufficient resolution for visualization of capillary structures and it can provide depth-resolved information. Flow, and vasculature by extension, can be visualized not only as an en-face projection, but also depth by depth or, more generally, cross-section by cross-section. Furthermore, different ranges of depth can be conveniently integrated to provide en-face angiographic visualizations corresponding to different zones along depth (e.g., superficial blood vessels, deep capillary plexus, choriocapillaris), all from a single 3D OCT scan process (including those involving repetitive scans, for example, as described below) with a scan time on the order of only several seconds. Compared with conventional angiography imaging modalities (e.g., fluorescein angiography (FA), and indocyanine green angiography (ICGA)), OCT angiography does not require exogenous dye which can induce adverse reactions in patients. In addition, the high signal to noise ratio (SNR) of OCT technology and high sensitivity and high contrast for flow detection enable OCT angiography to provide noninvasive, and high resolution/fidelity visualization of vasculature in both transverse and depth directions.

Generally, angiographic OCT techniques may be implemented by: (1) repetitively scanning each location within a 3D volume and analyzing the multiple repetitions at each scan location for motion; (2) incremental stepping between locations (i.e., not repetitively scanning each location), such that each location is sufficiently similar to the previous location to enable motion detection analysis; and (3) scanning at a very high resolution in the fast axis, such that there is overlap between successive A-lines; therefore, rather than comparing between corresponding locations in B-scans, adjacent A-lines can be compared to evaluate motion. Variants of the above methods have also been proposed, such as measuring several A-lines and then repeating before moving onward within the B-scan.

One example approach is optical microangiography (OMAG), which utilizes both OCT phase and magnitude information to deliver finely detailed angiographic images. Recently a variation of OMAG called Intensity Differentiation, which does not utilize phase information, has been proposed. Another example is split-spectrum amplitude-decorrelation angiography (SSADA), which uses only magnitude information in which spectral data is split into chunks that are separately processed based on an amplitude-decorrelation formula, and then later combined.

In OMAG, calculations are based on differences between intensity values. These difference calculations are implemented as subtractions between intensity terms, and in the case of complex operations, may be followed with taking the magnitude of the result.

With SSADA, the spectral bandwidth is split into smaller equally-sized bands. This is illustrated in FIG. 1, whereby the total bandwidth (BW) is split into four sub-bands (bw1, bw2, bw3, and bw4) to produce four interferograms I'(x,k') corresponding to each of the four sub-bands. For each sub-band: (1) A window function is applied; (2) Images are constructed; and (3) Angiographic calculations, using an amplitude-decorrelation formula, are performed between adjacent frames. Then, the decorrelations among all frame combinations are averaged. B-scans that might not match the other B-scans may be excluded. This can serve to reduce motion artifacts that manifest as bright lines that may span an en-face angiogram from one end to the other.

BRIEF SUMMARY OF THE INVENTION

According to one example, an angiographic OCT method comprises calculating ratio-based values of OCT images generated from captured OCT data of a subject volume, the OCT data being captured at a plurality of times and the values being calculated by comparing respective pixels of the OCT images at the plurality of times; generating angiographic images based on the values; and displaying, rendering, and/or storing the OCT images and/or the angiographic images, wherein when the values include ratio-based values, the ratio-based values are not further modified by a non-linear calculation.

In various embodiments of the above example, the ratio-based values are calculated according to a function that receives, as a variable input, a value corresponding to a ratio between two intensities; the value corresponding to the ratio is a difference between log-scale intensity information between two OCT images; the ratio-based values are represented by a ratio between two intensities; the ratio-based values are calculated by dividing first pixel values of an OCT image obtained at a first time by second pixel values of an OCT image obtained at a second time; the ratio-based values are substantially equivalent to or correspond to a ratio calculation of a pair or pairs of OCT images at the plurality of times; the ratio-based values are calculated for OCT images at at least two of the plurality of times; the method further comprises: averaging the ratio-based values for an X-Y position of the OCT images; comparing the averaged values to a criteria; and excluding ratio-based values that do not meet the criteria; the averaging, comparing, and excluding are performed A-line by A-line; the method further comprises filtering the captured data before generating the OCT images, before generating the angiographic images, and/or before displaying the OCT images and/or angiographic images, wherein the filter characteristics are customized based on the image to be generated or displayed by depth, depth size, or type of vasculature; the displaying includes displaying at least one high-resolution OCT image and/or OCT angiography image, and at least one filtered OCT image and/or OCT angiography image; the method further comprises generating the OCT images of the subject volume based on the captured OCT data; a partial spectrum of an OCT light source is used to generate at least one of the OCT images; OCT images are generated by applying a function to interferograms, or from interferograms having envelopes, and wherein an equivalent noise bandwidth (ENBW) for generating structural OCT images is greater than the ENBW for generating angiographic OCT images; the ENBW for generating angiographic OCT images is less than 1.23; the envelopes are of interferograms immediately before a discrete Fourier transform is applied; at least one of the values achieves a greater sensitivity to a decorrelation between OCT images at the plurality of times than a value determined according to $$1 - \frac{1}{N-1}\frac{1}{M}\sum_{n=1}^{N-1}\sum_{m=1}^{M}\frac{A_n(x,z)A_{n+1}(x,z)}{\left[\frac{1}{2}A_n(x,z)^2 + \frac{1}{2}A_{n+1}(x,z)^2\right]},$$

where N is the number of repeat B-scans, M is the number of spectral splits, and An and Am are pixel values in subsequent images; the values are enabled or utilized only for pixels having a value greater than a minimum intensity threshold; the minimum intensity threshold is determined by selecting a pixel intensity at a predetermined percentile of pixel intensities according to a histogram or sorted list of pixels of at least a portion of the OCT images; the pixel intensities only correspond to a background signal of the OCT images; the pixel intensities correspond to more than a background signal of the OCT images; A-scans of the OCT data are captured at a rate less than 1 MHz; and/or A-scans of the OCT data are captured at a rate between 25 kHz and 800 kHz.

According to another example, an angiographic OCT method comprises: calculating angiographic deviation values of OCT images generated from captured OCT data of a subject volume, the OCT data being captured at a plurality of times and the values being calculated by comparing respective pixels of the OCT images at the plurality of times; generating angiographic images based on the values; and displaying, rendering, and/or storing the OCT images and/or the angiographic images, wherein when the values include ratio-based values, the ratio-based values are not further modified by a non-linear calculation.

In various embodiments of the above example, the angiographic deviation values are calculated between images at the first time and at the second time; the angiographic values are calculated for OCT images at at least two of the plurality of times; the method further comprises: averaging the angiographic deviation values for an X-Y position of the OCT images; comparing the averaged values to a criteria; and excluding angiographic deviation values that do not meet the criteria; the averaging, comparing, and excluding are performed A-line by A-line; the method further comprises filtering the captured data before generating the OCT images, before generating the angiographic images, and/or before displaying the OCT images and/or angiographic images, wherein the filter characteristics are customized based on the image to be generated or displayed by depth, depth size, or type of vasculature; the displaying includes displaying at least one high-resolution OCT image and/or OCT angiography image, and at least one filtered OCT image and/or OCT angiography image; the method further comprises generating the OCT images of the subject volume based on the captured OCT data; a partial spectrum of an OCT light source is used to generate at least one of the OCT images; OCT images are generated by applying a function to interferograms, or from interferograms having envelopes, and wherein an equivalent noise bandwidth (ENBW) for generating structural OCT images is greater than the ENBW for generating angiographic OCT images; the ENBW for generating angiographic OCT images is less than 1.23; the envelopes are of interferograms immediately before a discrete Fourier transform is applied; at least one of the values achieves a greater sensitivity to a decorrelation between OCT images at the plurality of times than a value determined according to $$1 - \frac{1}{N-1}\frac{1}{M}\sum_{n=1}^{N-1}\sum_{m=1}^{M}\frac{A_n(x,z)A_{n+1}(x,z)}{\left[\frac{1}{2}A_n(x,z)^2 + \frac{1}{2}A_{n+1}(x,z)^2\right]},$$

where N is the number of repeat B-scans, M is the number of spectral splits, and An and Am are pixel values in subsequent images; the values are enabled or utilized only for pixels having a value greater than a minimum intensity threshold; the minimum intensity threshold is determined by selecting a pixel intensity at a predetermined percentile of pixel intensities according to a histogram or sorted list of pixels of at least a portion of the OCT images; A-scans of the OCT data are captured at a rate less than 1 MHz; A-scans of the OCT data are captured at a rate between 25 kHz and 800 kHz; and/or the angiographic deviation values are log-normal deviation values or geometric standard deviation values.

According to another example, a method comprises: calculating values of OCT images generated from captured OCT data of a subject volume at a plurality of times; and generating angiographic images based on the values.

In various embodiments of the above example, the values are ratio-based, angiographic deviations (e.g., log-normal deviations, geometric standard deviations), or combinations thereof; the values are calculated by comparing respective pixels of the OCT images at the plurality of times; the values are calculated according to a function that receives, as a variable input, a value corresponding to a ratio between two intensities; the value corresponding to the ratio is based on a difference between log-scale intensity information between two images; the values are not further modified by a non-linear calculation; a ratio-based value is not further modified by a non-linear calculation; the values can be represented by a ratio between two intensities; the values are calculated by dividing the pixels of an OCT image at a first time by the pixels of an OCT image at a second time, and the angiographic deviation values are calculated between images at a first time and at a second time; the values are calculated according to $$r(x, z) = \text{abs}\left(\log\left[\frac{A_m(x, z)}{A_n(x, z)}\right]\right)$$

or $r(x, z) = \text{abs}(\log[A_m(x, z)] - \log[A_n(x, z)])$, where abs( ) is an absolute value calculation, log( ) is a logarithm in any base, and m and n refer to any two images where m does not equal n; the values are substantially equivalent to or corresponding to a ratio calculation of a pair or pairs of OCT images at the plurality of times; the values are calculated for OCT images at least two of the plurality of times, the plurality of times being determined by any permutation of the plurality of times; the permutation is arbitrarily selected; the method further comprises averaging the ratio-based or angiographic deviation values for an X-Y position of the OCT images; comparing the averaged values to a criteria; and excluding ratio-based values that do not meet the criteria; the averaging, comparing, and excluding are performed A-line by A-line; the method further comprises averaging the ratio-based or angiographic deviation values; the ratio-based values or angiographic deviation values are averaged over a range within an A-line or across A-lines; the method further comprises displaying the OCT images and/or the angiographic images; the method further comprises filtering the captured data before generating the OCT images, before generating the angiographic images, and/or before displaying the OCT images and/or angiographic images; the filter characteristics are customized based on the image to be generated or displayed by depth, depth size, or type of vasculature; the display includes at least a 3D rendering visualization or high-resolution OCT image and/or OCT angiography image, and at least one filtered OCT image and/or OCT angiography image; the OCT image and/or OCT angiography image is an en-face image or B-scan; the method may instead comprise: capturing OCT data of a subject volume, the OCT data being captured at a plurality of times for at least one position in the subject volume; and generating OCT images of the subject area at the plurality of times; in generating the OCT images, no windowing function, a windowing function having an equivalent noise bandwidth (ENBW) less than 1.23, spectral reshaping having an ENBW less than 1.23, or any combination thereof is applied; structural OCT images are generated from interferograms of the OCT data having envelopes with an equivalent noise bandwidth (ENBW) greater than or equal to a predetermined level, and/or images for angiographic calculations are generated from interferograms of the OCT data having envelopes with an ENBW less than the predetermined level, wherein the envelopes are of interferograms immediately before a discrete Fourier transform is applied; a partial spectrum is used to generate the OCT images; structural OCT images are processed with a first set of parameters and images for angiographic calculations are processed with a second set of parameters; the first set of parameters includes a windowing function with an ENBW greater than or equal to 1.23, and the second set of parameters includes, a windowing function having an ENBW less than 1.23, spectral reshaping having an ENBW of less than 1.23, a combination thereof, or does not include a windowing function; at least one of the values achieves a greater sensitivity to decorrelation than a value determined according to $$1 - \frac{1}{N-1}\frac{1}{M}\sum_{n=1}^{N-1}\sum_{m=1}^{M}\frac{A_n(x, z)A_{n+1}(x, z)}{\left[\frac{1}{2}A_n(x, z)^2 + \frac{1}{2}A_{n+1}(x, z)^2\right]},$$

where N is the number of repeat B-scans, M is the number of spectral splits, and $A_n$ and $A_m$ are pixel values in subsequent images; the values are calculated only for pixels having a value greater than a minimum intensity threshold; the minimum intensity threshold is calculated relative to a weak foreground signal; the minimum intensity threshold is determined by selecting a pixel intensity at a predetermined percentile of pixel intensities according to a histogram or sorted list of at least a portion of the OCT images; the percentile is between 25-30% or 50-75% when the pixel intensities are ordered from least to greatest; the minimum intensity threshold is determined automatically according to predetermined pixel intensity percentile; A-scans are acquired at a rate less than 1 MHz; A-scans are acquired at a rate between 25 kHz and 800 kHz; and/or the angiographic deviation values are log-normal deviation values or geometric standard deviation values.

In still another example, an OCT system implements any of the above example methods. In various embodiments of such a system, a user is presented with angiographic data or images generated from at least two calculations or wherein the user is presented with an option to select which of at least two calculations to use to generate angiographic data or images.

It is noted that any combination of the above examples and embodiments thereof is within the scope of the present disclosure. The various embodiments of each example are not intended to be limited to that example, and may be applied to other examples or variations of those examples.

DETAILED DESCRIPTION OF THE DRAWINGS

Figure 1:
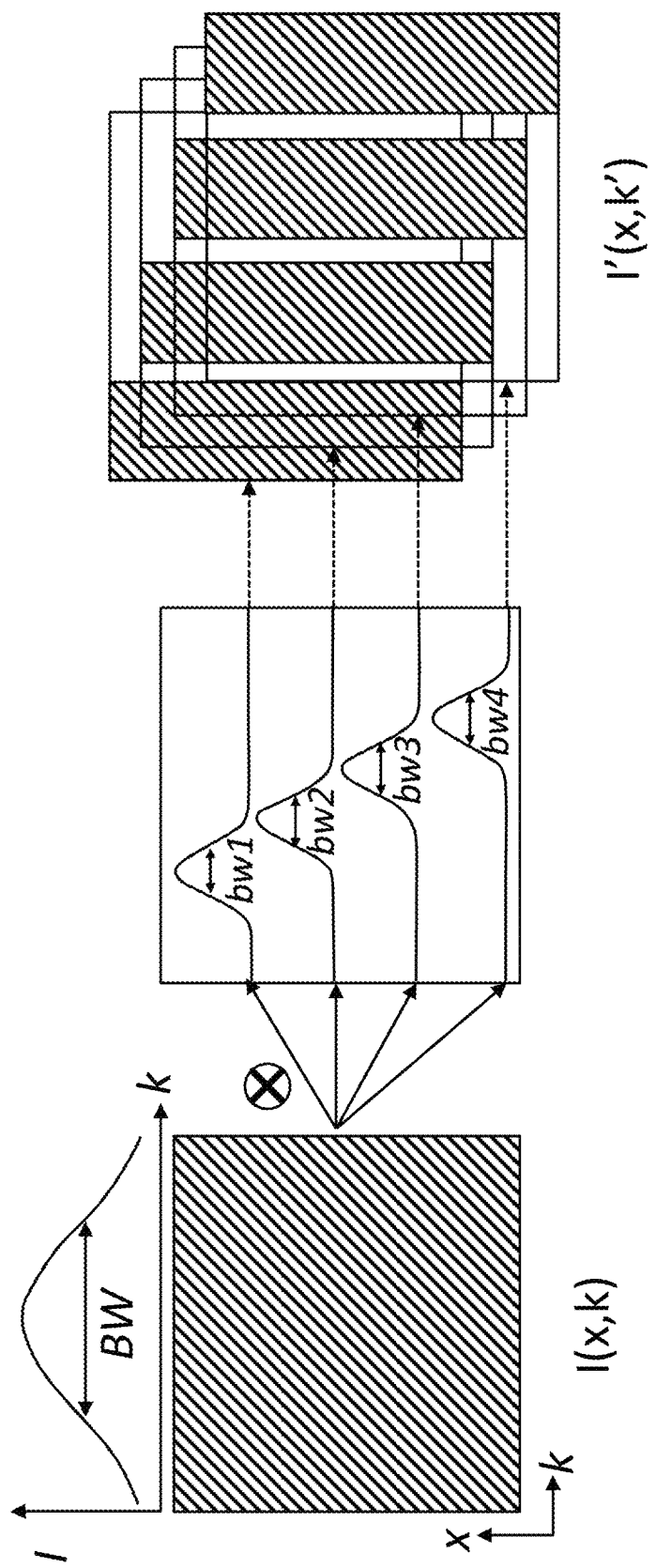
FIG. 1 illustrates a diagram of a Split-Spectrum Amplitude-Decorrelation Angiography (SSADA) technique.

Certain terminology is used herein for convenience only and is not to be taken as a limitation on the present invention. Relative language used herein is best understood with reference to the drawings, in which like numerals are used to identify like or similar items. Further, in the drawings, certain features may be shown in somewhat schematic form.

It is also to be noted that the phrase "at least one of", if used herein, followed by a plurality of members herein means one of the members, or a combination of more than one of the members. For example, the phrase "at least one of a first widget and a second widget" means in the present application: the first widget, the second widget, or the first widget and the second widget. Likewise, "at least one of a first widget, a second widget and a third widget" means in the present application: the first widget, the second widget, the third widget, the first widget and the second widget, the first widget and the third widget, the second widget and the third widget, or the first widget and the second widget and the third widget. Finally, the term "substantially," if used herein, is a term of estimation.

Figure 2:
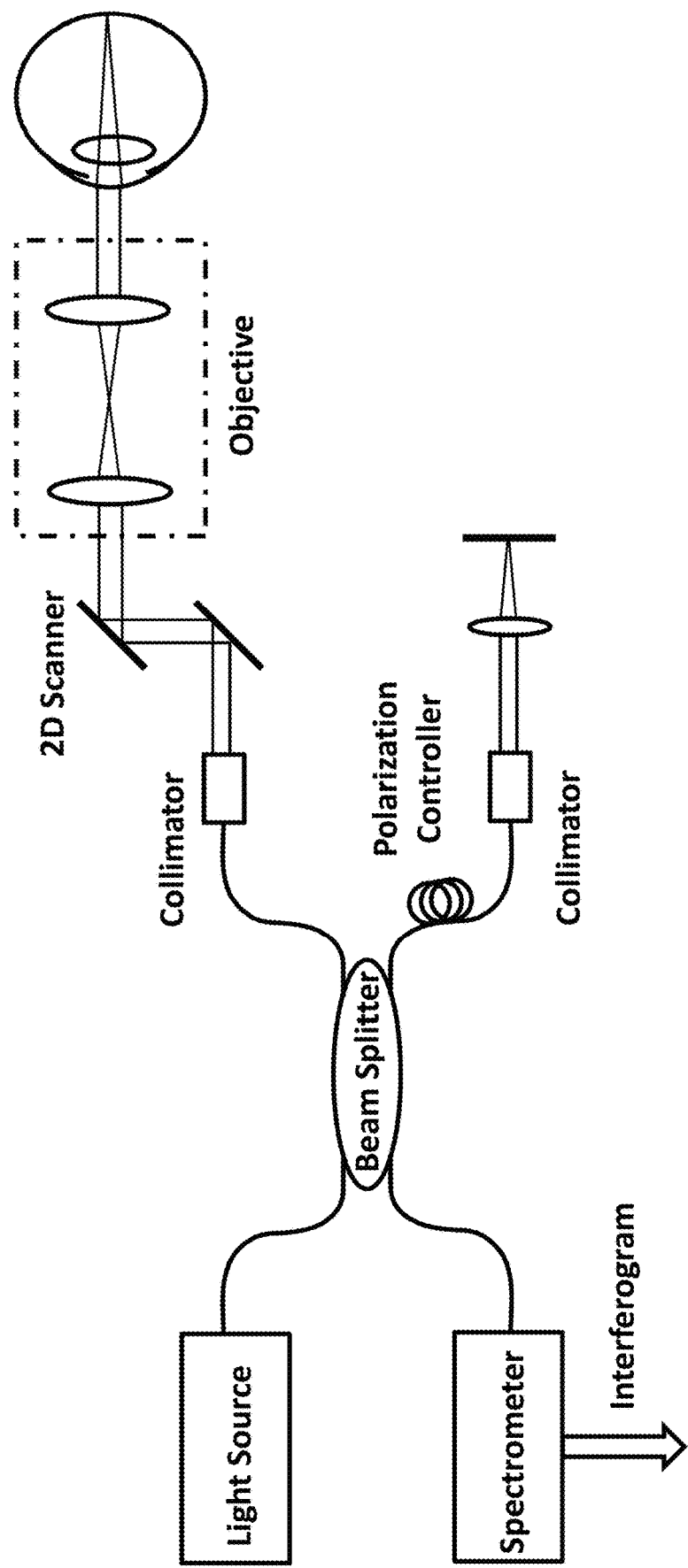
FIG. 2 illustrates a representative spectral domain optical coherence tomography (SD-OCT) system.
Figure 3:
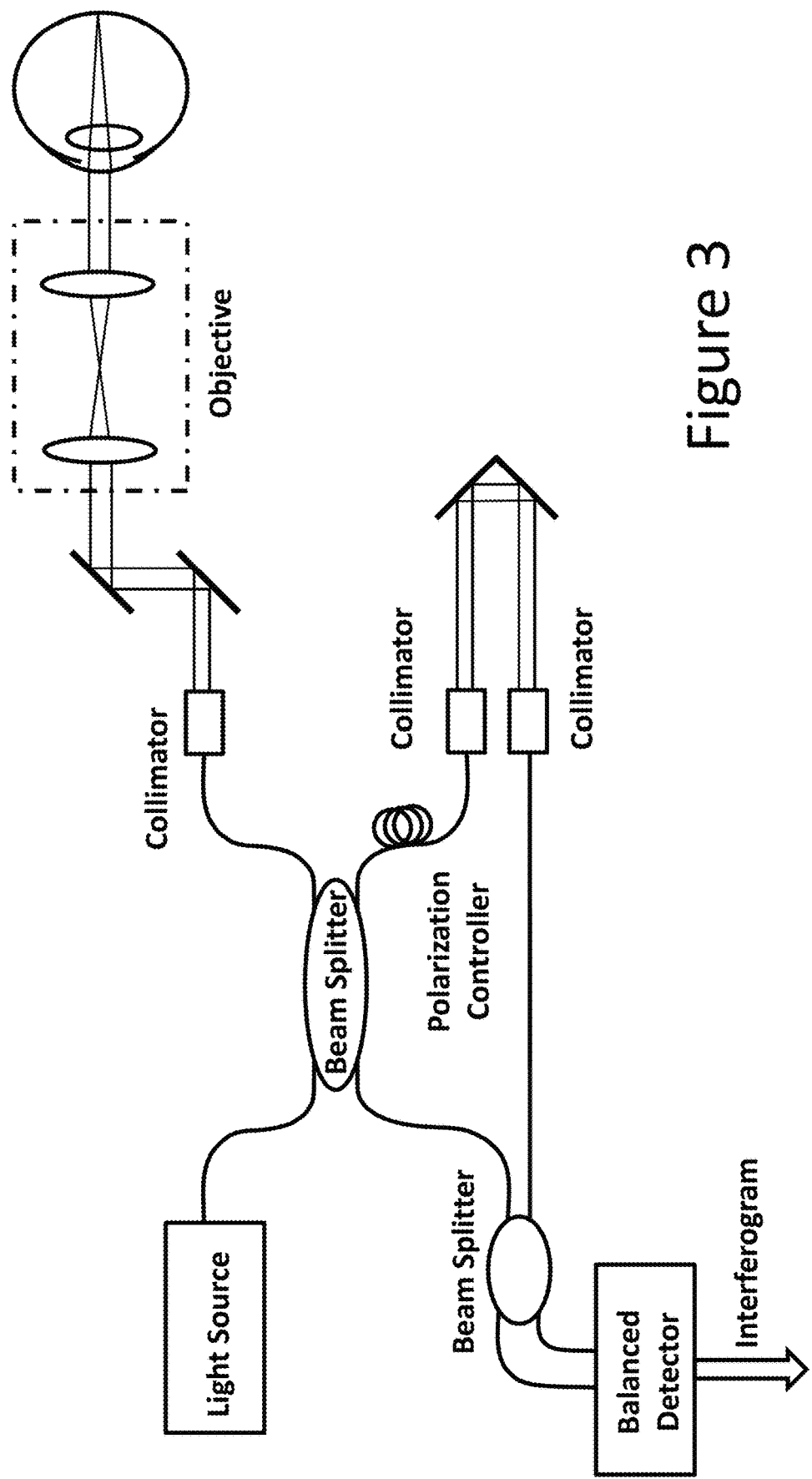
FIG. 3 illustrates a representative swept-source optical coherence tomography (SS-OCT) system.

It should be noted that the following description applies to Fourier domain OCT implementations, including both spectral domain OCT (SD-OCT) and swept-source OCT (SS-OCT) in any wavelength/frequency band. FIGS. 2 and 3 illustrate SD-OCT and SS-OCT systems, respectively, as are generally understood in the art. The SD-OCT examples provided herein are from about the 850 nm band and the SS-OCT examples provided herein are from about the 1050 nm band. Additionally, although for convenience the following disclosure references images and scan patterns in terms of horizontal B-scans in the X-Z plane, images and scans may have any arbitrary orientation. For example, the angiographic scans can be 3D horizontal scans, 3D vertical scans, 3D diagonal, raster scans, cross scans, circumpapillary, radial scans, or the like. Scan lines can be of arbitrary orientation, length, and curvature, and do not have to follow regular patterns or orientations relative to those in other neighboring scan locations.

It is also noted that although FIGS. 2 and 3 illustrate representative OCT systems, such specific systems are not required as part of the present disclosure. Rather, the present disclosure also pertains to data that has already been captured and/or OCT images that have already been generated. OCT images as used herein refer to any images formed based on OCT captured data, for example, A-scans, B-scans, and C-scans. Such data may have been captured with any type of OCT system, including time-domain OCT, or even other imaging modalities. In other words, the aspects described herein can also apply to fully processed OCT images. Accordingly, these aspects can be independent of the underlying OCT system optical design or other imaging modality.

In SSADA, a degree of decorrelation is calculated according to:

$$\overline{D}(x, z) = 1 - \frac{1}{N-1}\frac{1}{M}\sum_{n=1}^{N-1}\sum_{m=1}^{M}\frac{A_n(x, z)A_{n+1}(x, z)}{\left[\frac{1}{2}A_n(x, z)^2 + \frac{1}{2}A_{n+1}(x, z)^2\right]}$$

where N is the number of repeat B-scans, and M is the number of spectral splits. This equation produces values between 0 and 1 indicating a degree of decorrelation. In other words, a low value indicates a high degree of correlation between each set of values, and a high value corresponds to a low degree of such correlation. A high degree of decorrelation is then associated with motion and, by extension, with flow. In practice, SSADA suffers from a number of deficiencies. For example, the amplitude-decorrelation formula has traditionally limited the decorrelation calculations to be between adjacent frames. In other words, the interframe calculations in SSADA are limited to adjacent frame combinations. Additionally, because the OCT images are blurred in an early stage of processing, the angiographic data reflects the lower resolution (blur), and some features that otherwise may have been resolvable in the original data may no longer be distinguishable.

It is now recognized that a ratio of frames may be used to quantify motion. For example, the ratio may be determined according to:

$$r = \frac{A_n(x, z)}{A_m(x, z)}$$

where m and n refer to arbitrary frames within a set of frame captures for a given scan location.

In view of this recognition, a ratio-based and/or angiographic deviation calculation is used to determine change or motion according to a first aspect of a technique described herein. According to a second aspect described herein, arbitrary interframe permutations are used to determine change or motion. According to a third aspect described herein, post-calculated, non-linear results for projection visualization are averaged. According to a fourth aspect described herein, poor matches are eliminated on an A-line by A-line basis. According to a fifth aspect described herein, windowing functions may be customized to improve results. A sixth aspect described herein relates to the use of partial spectrums. A seventh aspect described herein relates to utilizing a minimum intensity threshold for determining which pixels to use in a ratio-based calculation.

Figure 4:
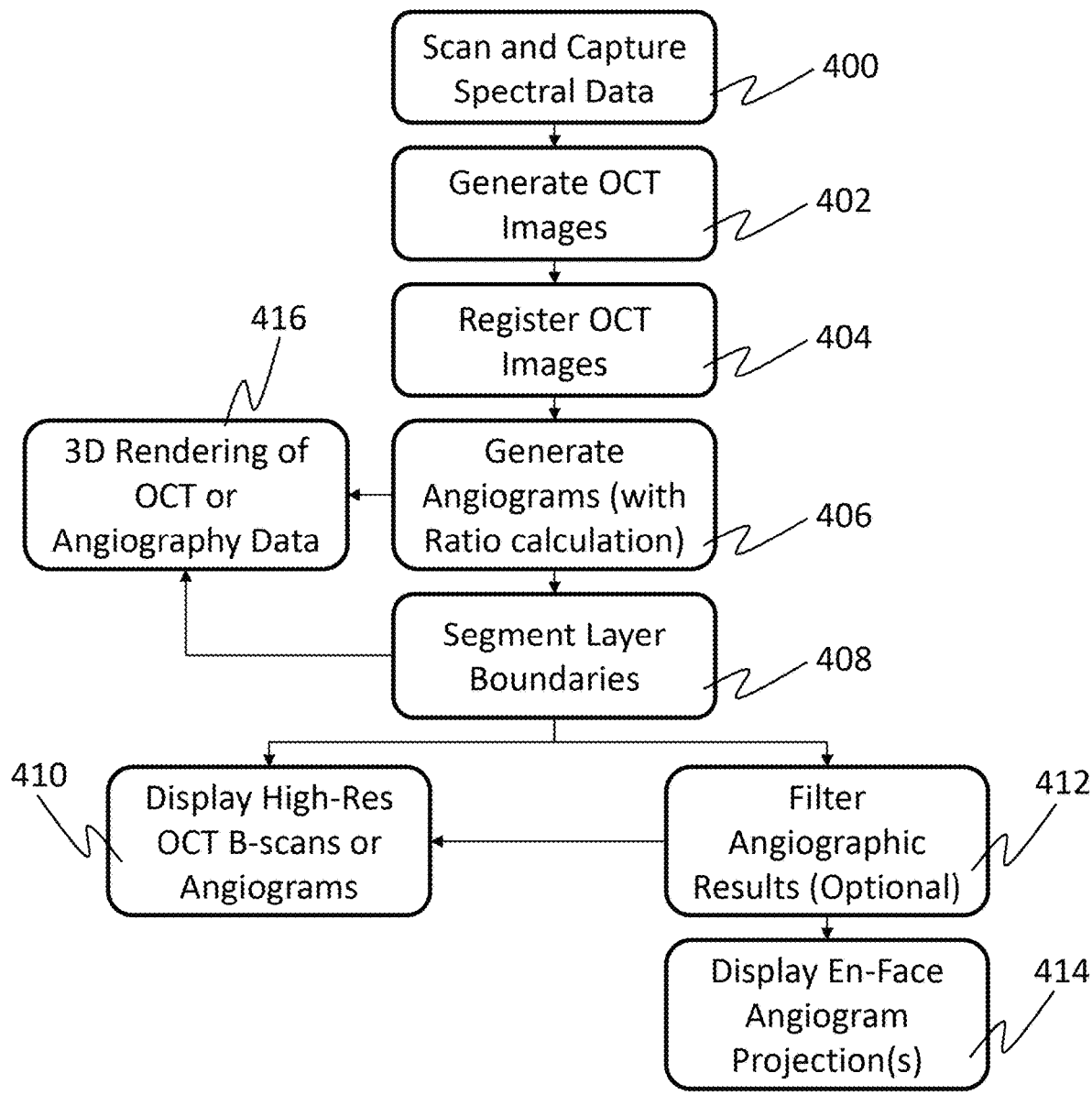
FIG. 4 is a flowchart of a technique described herein.

FIG. 4 illustrates a flowchart of a technique described herein according to the above aspects. It is noted that the various steps therein are optional, but each may be associated with improved results. According to a first step 400, spectral data is scanned and captured. Generally, a typical scan pattern may cover a 3 mm×3 mm area with 2-8 repetitions per scan line location for 512-1024 total B-scans (64 to 512 B-scan locations typically). It should be noted that such characteristics are not intended to be limiting and parameters such as the size of the scan pattern, repetitions per scan line, total number of B-scans, and total number of locations may be larger or smaller without deviating from the scope of the present disclosure.

Next, OCT images are generated from the captured data at step 402. Generating OCT images includes conventional processing to convert spectral (interferogram) data into OCT images. This may include, but is not limited to, one or more of rescaling (for example, with respect to SD-OCT data); fixed pattern noise (FPN) removal; numerical dispersion compensation (NDC); windowing; spectral reshaping; a discrete Fourier transform (DFT); magnitude and/or phase calculations; and/or logarithm conversion or other transform of magnitude data. It is noted that the various described steps that follow generally assume OCT intensity data in linear scale. Therefore, if data has been converted to log scale, it might be desirable to first convert back to linear scale for ratio calculations. Nevertheless, equivalent or corresponding logarithmic scale calculations may also be used.

In another optional step, frame repetitions at each scan location are registered with each other at step 404. In addition to aiding the angiographic process, the registration of the multiple frames, in combination with an averaging process, enables the generation of high-quality (improved SNR) B-scans that are potentially useful both for display purposes and segmentation purposes. The registration process may have the effect of reducing motion artifacts in the angiographic outputs, if saccadic or microsacaddic motion has occurred.

Before generating angiograms at step 406, OCT images may be preprocessed. For example, because angiography calculations are highly suspect to noise (e.g., Gaussian background or speckle noise), filters may be used to either disable or stabilize angiography calculations, for example in those pixels in which the signal intensity is relatively low compared to the background electrical noise. Filters such as a Gaussian filter may be utilized to filter data along A-lines, although a small degree of filtering across A-lines may also be applicable depending, for example, on the resolution of the scan. Several such methods can be used, alone or in tandem. In one example method, angiographic calculations may be disabled for pixels that do not meet a minimum intensity threshold level, either in the averaged composite image, or in the individual OCT frame. This minimum intensity threshold may be applied to individual frames, registered frames, averaged frames, and/or other forms of the captured data. According to an example application, pixel locations not meeting the minimum intensity threshold level may be assigned a value (e.g., 0 or some arbitrary value) as the angiographic result. Alternatively, the particular frame containing the affected pixel may be excluded from interframe calculations, for example, with respect to the given pixel. In another example, if any pixel intensity is below the threshold level, the pixel intensity may be saturated to a level of the threshold. In still another example, adding a "DC offset" to image pixel intensities can limit the degree that variations, which may be due to noise, affect the angiography calculations. When a positive constant DC offset level is added to both numerator and denominator in a ratio calculation, the result will tend to be moderated. In still other examples, a ratio may be calculated for pixels with signal intensities below the minimum intensity threshold, but only after all pixel values are raised to a predetermined level. This may have the effect of at least partially overcoming deconstructive speckle and bringing the ratio closer to unity.

Following preprocessing, selected (or potentially all) frame combinations at a particular scan location are processed to generate angiograms at step 406. Interframe calculations are applied on a pixel by pixel basis (e.g., in pairs of frames). In addition to the SSADA amplitude decorrelation calculation discussed above, other functions such as absolute difference, standard deviation, variance, coefficient of variation, maximum, median, geometric median and minimum are also conceivable. These functions may be applied in pairs of frames, per pixel, and/or combinations thereof. For example standard deviation and coefficient of variation, calculations may be performed among all frames to be included in a single calculation (per pixel) rather than being performed in a pair-wise manner between frames, they. Thus, the value for each pixel in the final, composite image represents an average among the individual calculations corresponding to the potentially multiple interframe combinations. These calculations may all be based on the post-registered images.

According to the first aspect, OCT angiographic results described herein are produced by a ratio-based calculation, thereby allowing sharp visualization of vasculature across the depths of the retina. Some ratio calculation methodologies require a one-sided ratio as an input. A one-sided greater ratio is a ratio of $A_1$ to $A_2$ if $A_1 \geq A_2$, or the ratio of $A_2$ to $A_1$ if $A_2 > A_1$, where $A_1$ and $A_2$ are pixel values of a given location in two images (at two points in time). Similarly, a one-sided lesser ratio (the inverse of the one-sided greater ratio) is the ratio of $A_1$ to $A_2$ if $A_1 \leq A_2$, or the ratio of $A_2$ to $A1$ if $A_2 < A_1$. Therefore, the one-sided greater ratio will always be greater than or equal to one, and the one-sided lesser ratio will always be between 0 and 1 inclusive, as long as $A_1$ and $A_2$ are both positive. The two types of one-sided ratios can be converted to one another by taking the reciprocal, as long as neither $A_1$ nor $A_2$ were zero. Either of these ratios can be pre-defined to have a fixed value of either one or some other value, should either or both of the $A_1$ or $A_2$ intensity values be equal to zero. The directionality of the ratio has no particular meaning.

It is noted that a one-sided ratio may also result from calculations other than simple division. For example, the ratio may result from taking the absolute value as described below with respect to the "log-ratio" method (effectively corresponding to a one-sided greater ratio). According to another example, the ratio may be the result of subtracting log-scale intensity information between images (as dividing two values and taking the logarithm is equivalent to subtracting two log-scale values; a one-sided ratio if the absolute value is taken). In this way, the ratio-based value can be a value other than a simple division of intensities. For example, the ratio-based values may be generated by operations other than division, including multiplications and exponentials (e.g., squaring). These various operations may be performed before or as part of the ratio-based calculation. In doing so, the operations do not necessarily affect a final sensitivity. Still other transformations may be applied following the ratio-based calculation.

In methodologies utilizing a one-sided ratio calculation, the calculated value may be saturated at a given level at an upper or lower range. It is possible to apply a fixed saturation level (e.g., a saturation level of 2, where one-sided greater ratio results are typically less than 2), such that constraining the result range may reduce storage requirements and improve data processing and visualization processing speeds.

The ratio value may be calculated according to any number of methods without diverting from the scope of the present disclosure. In a first approach, a "ratio as is" is calculated as a one-sided greater ratio value without any additional calculations or transformations. Accordingly, the "ratio as is" methodology directly compares a pixel value at a given location between two images (or frames). The analysis can be performed on a one-by-one location-by-location basis where both images are represented in a linear scale.

Figures 5, 6:
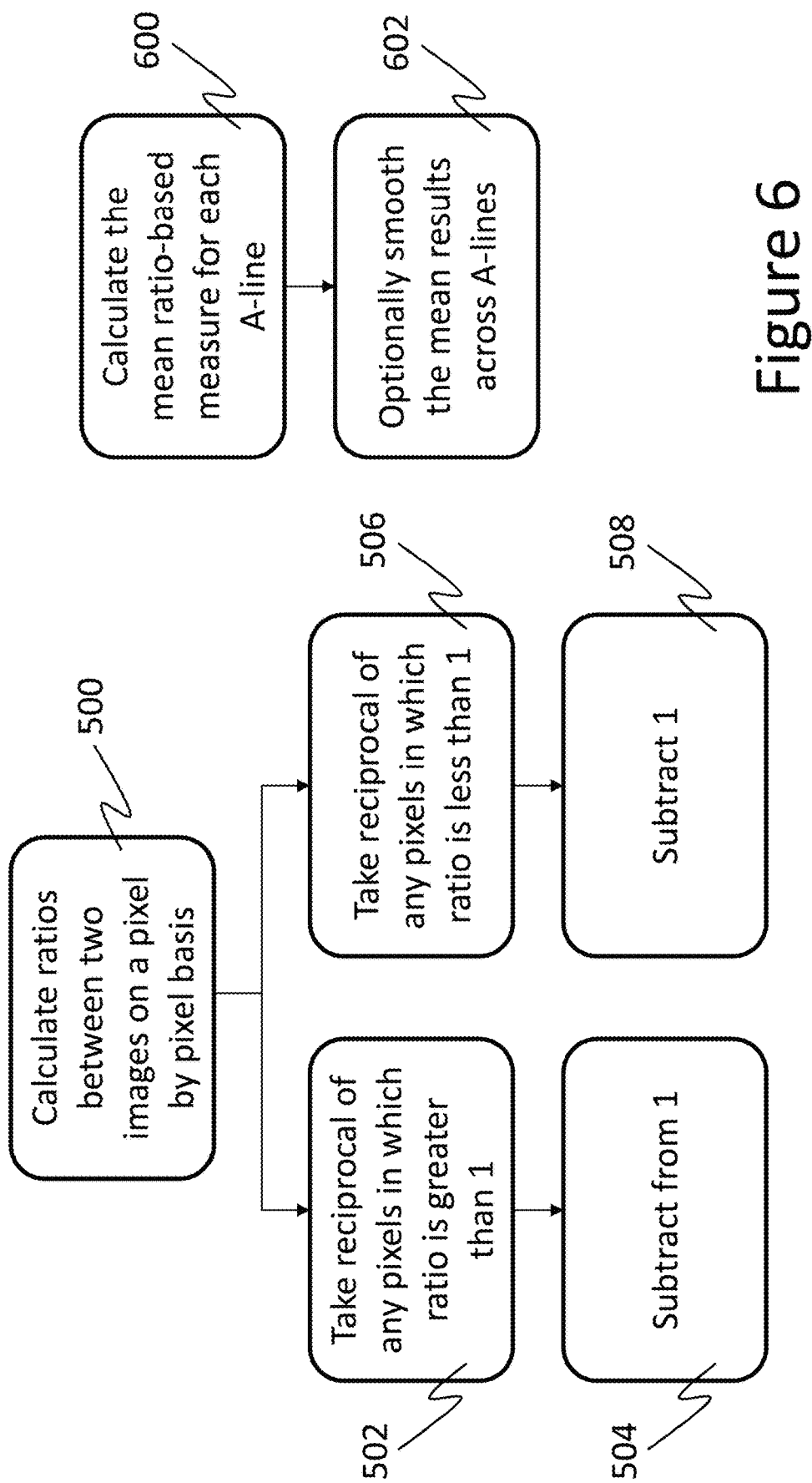
FIG. 5 is a flowchart for calculating a ratio-based value according to two methods.
FIG. 6 is a flowchart for quantifying motion artifacts.

Two other approaches to the ratio-based calculations are illustrated in FIG. 5. It is to be noted that the calculations illustrated in FIG. 5 assume images in linear scale. According to a first step of these calculations 500, the pixel values in one image are divided (thereby forming ratios) by those of the other image in the frame pair on a one-by-one location-by-location basis, where both images are represented in linear scale. If a pixel in the other image (the denominator) has a value of 0, then the calculated pixel result may be assigned an arbitrary value. It is noted that the ratio is a one-sided variable and the directionality of the ratio has no particular meaning. Thus, according to an "inverted ratio", at step 502 the reciprocal is taken for any pixels in which the ratio is initially greater than 1, so that the resulting ratios are between 0 and 1. This results in a one-sided lesser ratio, which can be subtracted from 1 at step 504 to generate an inverted ratio value. This approach may be generalized according to:

$$r(x, y) = 1 - \frac{1}{N} \sum_{i,j}^{N} \frac{\min(I_i(x, y), I_j(x, y))}{\max(I_i(x, y), I_j(x, y))}$$

where I(x, y) is the OCT signal intensity, N is the number of scanned B-scan combinations at the given location, and i and j represent the two frames within any given combination of frames. An averaging function could alternatively be implemented by any number of operations, including a median or other quantile, minimum, maximum, or geometric mean, for example, as described below.

Similarly, according to a "ratio minus one" method, for pixels in which the ratio is less than 1, the reciprocal may be taken at step 506 should it be desired to obtain ratio values between 1 and infinity. This results in a one-sided greater ratio, from which 1 can be subtracted at step 508 to generate a ratio minus one value. This approach may also be generalized in a similar manner to the "inverted ratio" method.

In another approach, a "log-ratio" method, the ratio based calculation is performed according to:

$$r(x, z) = abs\left(\log\left[\frac{A_m(x, z)}{A_n(x, z)}\right]\right)$$

where the ratio is found by taking the absolute value of the log of the ratio of a frame pair. This is also equivalent to taking the logarithm of the one-sided greater ratio. The logarithm can be in any base, and m and n refer to any two images (where m does not equal n). In addition, a threshold can be optionally applied to the log-ratio result, such that, for example, any absolute values greater than 1 are saturated at that level. The logarithm calculation may be performed in any base because the relative results will be equivalent. Still, depending on the parameterization of the display step 410 (discussed below), the choice of logarithm base could be impactful. However, the display processing may be normalized to counteract the effect of the selected base.

It is noted that other variations of these calculations are conceivable without departing from the scope of the present disclosure. For example, one may take the logarithm of images before calculation, and then perform a subtraction rather than a division. This could be followed by taking the absolute value. Given the characteristics of logarithms, such a calculation would be equivalent to the above calculation. In other words, as noted above, dividing two values and taking the logarithm is equivalent to subtracting two log-scale values and taking the absolute value generates a one-sided ratio. For example:

$$r(x, z) = abs(\log[A_m(x, z)] - \log[A_n(x, z)])$$

However, because calculating the ratio with logarithms is not a calculation in the linear scale, performing further non-linear statistical calculations can greatly lower the relative sensitivity to areas with lower flow. For example, if the above calculation were further squared, the relative sensitivity would be squared. For values less than one (e.g., 0.011 as illustrated in Table 1), the squared value would be smaller by about a factor of 100 ($0.011^2$=0.000121). Such sensitivity is comparatively worse than linear calculations and amplitude decorrelation methods.

In this way, it is noted that calculations (e.g., functions) that utilize a ratio value as an input are also within the scope of the present disclosure. Such functions may take the form of f(r). However, still other functions may that do not explicitly recite ratio as an input variable are considered within the scope of the present disclosure. For example, a function defined as $f(A_1, A_2)=(A_1-A_2)/A_1$ divided through by $A_1$ in the denominator transforms to the function to f(r)=1−r or 1−(1/r), depending on the definition of r. Accordingly, this function can be represented as a function of the ratio as is to be understood herein. The above example is not intended to be limiting and still other similar functions are understood to be within the scope of the present disclosure. In still other embodiments, utilizing a value representative of a ratio is also within the scope of the present disclosure. For example, a magnitude of the ratio of two intensities multiplied by a phase term may be represented as a ratio. Similarly, for example, the magnitude difference between two log-scale intensities multiplied by a phase term is also within the scope of the present disclosure.

It is also noted that the above ratio calculations and the use of the above ratios can accommodate intensity data in the complex realm. In such cases, it is possible to take the magnitudes of each intensity before calculating the ratio, or calculate the complex ratio followed by a magnitude calculation. When in the complex realm, it is conceivable to utilize the complex conjugate (or other similar numerical transformations) for either or both values in the ratio calculation.

Furthermore, the ratio can be generalized and expanded to include an angiographic deviation, such as a geometric standard deviation or log-normal deviation (a standard deviation of a log-normal distribution). Still further, the angiographic deviation can be generalized and expanded to include calculations (e.g., non-ratio calculations, such as a variance) that provide results similar or equivalent to standard deviations. For example, taking the average of a series of pairwise absolute differences (or differences to the collective mean) will roughly correspond to the (arithmetic) standard deviation or absolute deviation, and taking the average of a series of pairwise ratio measures will roughly correspond to the geometric standard deviation, for example, with respect to angiographic visualizations as discussed herein. Therefore, taking a standard deviation is roughly analogous to taking the sum of the absolute values of pairwise differences, and taking the geometric deviation of the corresponding pixel values in the component image frames is roughly analogous to the pairwise ratio methodology discussed previously and can achieve similar results. It is noted that ratios, by their nature, are calculations based on pairs of data; geometric standard deviations can be performed using any number of frames.

The angiographic deviation is also understood to be a log-normal deviation. For example, a log-normal deviation results from log-scale images where a standard deviation is calculated among all frames for each pixel location of the log-scale images. This log-normal deviation can produce results similar to a geometric standard deviation taken on linear scale images, and thus can also produce results similar to taking the difference of logarithms, as discussed above.

An angiographic deviation may also refer to still other calculations that produce results similar or equivalent to any of the above described calculations, such as an absolute deviation and/or variance. It is noted that the above-described angiographic deviations can be used in addition to, or alternatively to, the above-described ratio-based methodologies.

Nevertheless, the calculations can be flexibly applied without significantly affecting the results. For example, the arithmetic mean or another averaging technique could be utilized in place of a geometric mean. Similarly, the ratio calculations could be implemented using the pixel-wise ratios between each image frame and a collective mean image (either an arithmetic or geometric mean, or similar averaging technique), and averaging across results (also arithmetic or geometric mean, or similar averaging technique). The order of the geometric standard deviation calculation could also be altered. For example, the component images can be multiplied by any given factor or the image pixels may be transformed, for example, by a power operation.

While the above examples relate to inputting a ratio or pixel value to an algorithm, it is also possible to implement the above calculations in a more digital form. For example, a lookup table may be utilized, where pre-determined outputs corresponding to given inputs are stored, e.g., in memory of the system on which the present disclosure is implemented. Such a table could also be stored remotely.

The following table illustrates a comparison of sensitivities (indicated relative to the values of other rows in the same column, rather than across columns) of the above described log-ratio, inverted ratio, and ratio minus one results to the amplitude decorrelation calculation over a range of one-sided greater ratio values (left column).

TABLE 1

Comparison of relative sensitivities within various calculations

| One Sided Greater Ratio | Log-Ratio Method | Inverted Ratio Method | Ratio Minus 1 Method | Amplitude Decorrelation |
|---|---|---|---|---|
| 1.000 | 0.000 | 0.000 | 0.000 | 0.0000 |
| 1.025 | 0.011 | 0.024 | 0.025 | 0.0003 |
| 1.050 | 0.021 | 0.048 | 0.050 | 0.0012 |
| 1.100 | 0.041 | 0.091 | 0.100 | 0.0045 |
| 1.250 | 0.097 | 0.200 | 0.250 | 0.0244 |
| 1.500 | 0.176 | 0.333 | 0.500 | 0.0769 |
| 2.000 | 0.301 | 0.500 | 1.000 | 0.2000 |
| 3.000 | 0.477 | 0.667 | 2.000 | 0.4000 |
| 4.000 | 0.602 | 0.750 | 3.000 | 0.5294 |
| 5.000 | 0.699 | 0.800 | 4.000 | 0.6154 |
| 7.500 | 0.875 | 0.867 | 6.500 | 0.7380 |
| 10.000 | 1.000 | 0.900 | 9.000 | 0.8020 |

As can be seen, the ratio-based methods are more sensitive to ratios closer to 1 (e.g., the 1.025-1.10 one-sided greater ratio rows of the tables) than is amplitude decorrelation. The result of this is increased sensitivity to and linearity with respect to less flow. The results for the ratio-based methods are also significantly greater when viewed relative to greater flows (higher one-sided greater ratio values). As noted above, the linear ratio methods (Inverted Ratio and Ratio Minus 1) provide better relative sensitivity characteristics at low and moderate-to-high flows than the Log-Ratio method. It should be noted that this table, and all following tables, could alternatively be presented in terms of one-sided lesser values.

The following tables illustrate relative "within-method" results for a given function when evaluated relative to a stated reference ratio. In other words, the following tables illustrate the sensitivity within a single method at different flow levels as compared to the reference ratio level. For example, the amplitude decorrelation value of 80.02 for a one-sided greater ratio value of 1.025 is obtained by: 0.0244/0.0003 (accounting for rounding) as found in Table 1. Accordingly, a low value indicates better sensitivity of low-flow detection.

TABLE 2

Relative within-method sensitivity of low flow based on a reference ratio of 1.250

| One Sided Greater Ratio | Log-Ratio Method | Inverted Ratio Method | Ratio Minus 1 Method | Ratio As Is | Amplitude Decorrelation |
|---|---|---|---|---|---|
| 1.025 | 9.04 | 8.20 | 10.00 | 1.22 | 80.02 |
| 1.050 | 4.57 | 4.20 | 5.00 | 1.19 | 20.51 |
| 1.100 | 2.34 | 2.20 | 2.50 | 1.14 | 5.39 |
| 1.250 | 1.00 | 1.00 | 1.00 | 1.00 | 1.00 |

TABLE 3

Relative within-method sensitivity of low flow based on a reference ratio of 1.500

| One Sided Greater Ratio | Log-Ratio Method | Inverted Ratio Method | Ratio Minus 1 Method | Ratio As Is | Amplitude Decorrelation |
|---|---|---|---|---|---|
| 1.025 | 16.42 | 13.67 | 20.00 | 1.46 | 252.38 |
| 1.050 | 8.31 | 7.00 | 10.00 | 1.43 | 64.69 |
| 1.100 | 4.25 | 3.67 | 5.00 | 1.36 | 17.00 |
| 1.250 | 1.82 | 1.67 | 2.00 | 1.20 | 3.15 |
| 1.500 | 1.00 | 1.00 | 1.00 | 1.00 | 1.00 |

As can be seen, each of the ratio-based methodologies achieves a significantly greater sensitivity of low flow detection than amplitude decorrelation.

In comparing the calculations described herein with amplitude decorrelation, the comparison may be made based on the same number of split spectrums. As noted above, SSADA is calculated in part based on the number of spectral splits of the light source; and as the various calculations described herein can also utilize split spectrum processing, the most relevant comparisons compare sensitivities of each method utilizing the same number of spectrum splits. For example, the sensitivity of an amplitude decorrelation calculation using a spectrum split into two bands finds its relative comparison in other calculations also using two split bands.

The following tables illustrate relative advantages of ratio-based methodologies over amplitude decorrelation based on the "within-method" sensitivity of low flows. In other words, the following tables demonstrate the advantage of the ratio-based calculations using direct comparisons to the results from corresponding amplitude decorrelation calculations. For example, the "ratio as is" value of 65.62 for a one-sided greater ratio value of 1.025 for a reference ratio of 1.250 is obtained by: 80.02/1.22 (accounting for rounding) as found Table 2. Accordingly, larger values indicate a stronger relative advantage with respect to amplitude decorrelation.

TABLE 4

Relative advantage over amplitude decorrelation for a reference ratio of 1.250

| One Sided Greater Ratio | Log-Ratio Method | Inverted Ratio Method | Ratio Minus 1 Method | Ratio As is |
|---|---|---|---|---|
| 1.025 | 8.36 | 9.76 | 8.00 | 65.62 |
| 1.050 | 4.48 | 4.88 | 4.10 | 17.23 |
| 1.100 | 2.30 | 2.45 | 2.16 | 4.74 |
| 1.250 | 1.00 | 1.00 | 1.00 | 1.00 |

TABLE 5

Relative advantage over amplitude decorrelation for a reference ratio of 1.500

| One Sided Greater Ratio | Log-Ratio Method | Inverted Ratio Method | Ratio Minus 1 Method | Ratio As is |
|---|---|---|---|---|
| 1.025 | 15.37 | 18.47 | 12.62 | 172.46 |
| 1.050 | 7.78 | 9.24 | 6.47 | 45.28 |
| 1.100 | 4.00 | 4.64 | 3.40 | 12.47 |
| 1.250 | 1.74 | 1.89 | 1.58 | 2.63 |
| 1.500 | 1.00 | 1.00 | 1.00 | 1.00 |

Some implementations of the present disclosure may simultaneously support calculating different numerical measures corresponding to motion variation. For example, each (or any two) of the measures in the above tables could be simultaneously calculated with the results available to a user. Thus, the user may be shown similar calculations with different degrees of sensitivity and noise characteristics that may be selected as desired. In other embodiments, an interface could be provided that allows the user to select which one (or more than one) of the multiple calculations to perform. While the above table discloses a few ratio methods and amplitude decorrelation, it is noted that these calculations are not intended to be limiting. For example, other calculations may include variance, standard deviation, coefficient of variation, absolute difference, and the like. More generally, it is noted that the above calculations are based on arithmetic differences and arithmetic deviation, whereas ratio and geometric deviation calculations are based on geometric differences and deviations. Therefore, providing both geometric and arithmetic calculation results simultaneously to a user may provide independent, useful information.

As discussed above, interframe combinations are based on those frames that are scanned consecutively (adjacent in time). Such combinations have a minimal separation of time, allowing for high flow rates to be captured via the interframe calculation, which may yield high calculation sensitivity. Additionally with such combinations, frames can be more likely optimally matched to one another both with and without registration (keeping in mind that the eye is frequently in motion). Different time separations can uncover or emphasize different information within the resulting angiograms. For example, longer time intervals allow for visualization of slower flow. However, such interframe calculations are still fixed separations in time. Further, given eye motion (e.g., including saccades, microsaccades, and bulk motion that might in some cases affect the cornea, pupil, and vitreous in addition to the retina) and possibly other distortions in the imaging process (e.g., including phase instability and/or positioning error within the OCT system), the flexibility to include arbitrary combinations of frames can improve results by making calculations available when there otherwise might be none (or very limited).

Thus, according to the second aspect described herein, any arbitrary permutation of interframe combinations, regardless of their time separation, may be used to determine the above ratio-based calculation. For example, with the case of four repetitions, only those separated by one frame (leading to three combinations of N and N+1; N+1 and N+2; and N+2 and N+3), those separated by two frames (N and N+2; and N+1 and N+3), those separated by three frames (N and N+3), or any arbitrary combination of any of these pairings (that may or may not include all the pairings for a given frame separation) may be utilized. Therefore, if all frame combinations were to be used in this four repetition example scenario, there would be a total of six different interframe combinations. However, more generally any of the 63 possible permutations that include any number of these six different interframe combinations (still in this four repetition example scenario) could be selected. That is, 6(N=1)+15(N=2)+20(N=3)+15(N=4)+6(N=5)+1(N=6)=63.

Referring back to FIG. 4, following angiogram calculation, the next step 408 includes boundary segmentation. Segmentation may be performed in a traditional manner, and may follow any of three permutations for angiographic 3D OCT volumes. First, segmentation of the registered and averaged frames (that represent a combination of the multiple repetitions at each scan location) may be advantageous due to the improved SNR associated with these images. Second, segmentation of the individual, non-averaged frames could be advantageous as results from individual frames could be used to detect and correct errors in other corresponding (or even nearby) frames. This may be performed based on the registered frames. Third includes segmentation of only those non-averaged frames that served as the templates for the registration process.

According to the third aspect described herein, angiographic results may be filtered at step 412, in part, to improve signal to noise ratio (SNR) in angiographic projection images and other displays. According to one example, an optional filter may be applied over the pixels within each A-line representing angiographic results. Such a filter could utilize, as an example, a Gaussian transfer function, or it could also be implemented via a moving average function, although such examples should not be seen as limiting as any kind of filter could be utilized. Depending on the resolution of the scan, the filter may also extend across A-lines.

The associated improvement in SNR is at least partially attributable to the fact that the ratio calculation is non-linear in nature (e.g., it is typically not linear to the pixel intensity values in any of the individual image frames used to generate the ratio result). Then, by smoothing and/or averaging the ratio results (or any results based on a non-linear calculation for that matter), the SNR of the composite angiographic results can be improved. It should be noted that due to the non-linear nature of the ratio as well as some other angiographic calculations (including amplitude decorrelation), this type of filtering/smoothing/averaging will be more impactful towards angiographic SNR improvements than is filtering precursor OCT images in a similar manner (as described above). In other words, it may actually be deemed desirable to leave OCT images in the highest resolution possible, and then apply the filter/smoothing/averaging step at this point to the angiographic output data, thereby achieving a best case scenario of high resolution structural and angiographic data while also being able to demonstrate filtered results in terms of projection views.

In one embodiment of the third aspect, a Gaussian filter with a sigma of approximately 8 microns is utilized, although it should be noted that this filter can be narrower or wider while achieving similar results and staying within the scope of the present disclosure. This filter may also, or alternatively, be applied as a pre-processing step to any projection visualizations. Thus, the filter will not necessarily affect the base data results and/or the high-resolution display(s). Additionally, it is noted that the filter parameters (e.g., type and length) may be customized to the depth and type of the vasculature being displayed. For example, projections covering a wide depth or of larger vasculature may justify larger filter sizes with broader bandwidths, while projections representing narrower layers of capillaries may be better served by relatively smaller and narrow filter sizes. Since multiple projection views may be displayed simultaneously, multiple sets of filter parameters may also be used at one time.

Artifacts that result from subject eye motion and other factors including OCT system phase stability and/or positioning errors are a common source of image degradation in processed OCT angiography results. While either tracking or motion compensation may serve as valuable methods to reduce or eliminate such motion artifacts, it may also be desirable to be able to make the most of existing captured data, as this may result in a simpler scan protocol that ultimately takes less time and is easier on the imaging subject. It is possible to detect relatively increased motion on an A-line by A-line basis utilizing mean ratio values across A-lines (i.e., no need for a priori segmentation). FIG. 6 illustrates such a method.

According to FIG. 6, for each frame combination, the mean ratio-based measure is calculated for each A-line 600 and then the mean results across A-lines may be smoothed at step 602. The mean ratio-based measure (may be any sort of measure, also including amplitude decorrelation) is integrated or averaged over the depth of the A-line. If segmentation data were available, the data could be utilized to limit the integration or averaging depth. In other embodiments, the calculation in step 600 could be, for example, the median or an arbitrary quantile rather than the mean. The results over a number of neighboring or nearby A-lines may be averaged, filtered, or smoothed at step 602 because calculation results in any one A-line may be subject to a degree of noise and randomness, and because motion is expected to be highly correlated over a relatively small number of A-lines (for a 100 kHz OCT system, for example, the time associated with each A-line is just 10 μsec). For example, a Gaussian filter can be applied, or a moving average may be calculated across A-lines; however, such a filter or average is not intended to be limiting.

According to the fourth aspect described herein, for each A-line, frame combinations associated with the lowest mean ratios are assumed to match the best with one another and are, therefore, deemed to be the least likely to have been affected by motion of any sort. The various component frame combination results can be sorted from lowest (best match) to highest (worst match), and various methods can then be applied to remove frame combinations from the overall angiographic calculation for that particular A-line. For example, in one embodiment, an absolute threshold may be applied, such that any pairs with mean ratios above such threshold are excluded from further use. According to another embodiment, a relative threshold—for example, averaging the best and worst results—can be utilized in a similar manner to what is described above. In still another embodiment, the top N pairs may be selected, thereby removing a fixed number of pairs representing the worst matches.

In still another embodiment, the list of frame combination results may be grouped using a technique such as Otsu's method to minimize variance between groups. Any entries in the group with the higher motion quantification results may be excluded from the angiographic calculations. Alternatively, a minimum number of entries in the group to be included may be specified.

In still another embodiment, the sorted list of results can be traversed one by one from the best to the worst matching results. For each step in the traversal, the two component frames used in the result calculation are noted. The two component frames of the next-best result (if any) are again noted, and the process is continued. Once all component frame numbers are encountered at least once, the routine stops and only those frame combinations encountered thus far in the traversal are included when averaging the angiographic calculations across the frame combinations. Optionally, the routine may in some cases go back or go forward one or more steps in the traversal process.

It is also noted that one or more of the above methods may also be combined into hybrid methods. For example, an absolute threshold can be applied, but there also may be a stipulation that at most n entries are included (or a minimum of n entries).

Following segmentation at step 408 and/or filtering at step 412, the angiograms or B-scans may be displayed at step 410. Optionally, in step 416, the OCT or angiographic data may be rendered, for example, in 3D following generation of the angiograms at step 406 and/or segmentation of the layer boundaries at step 408. The data may be displayed in numerous manners, including 3D rendering, arbitrary cross-sections including the X-Z and/or Y-Z plane (cross-section view), the X-Y plane (en-face), and/or any arbitrary combination (i.e., simultaneous views). Planes may also be sliced so as to not be in or orthogonal to the arbitrary X-Z, Y-Z, and/or X-Y planes. These displays may be filtered and/or smoothed; however, this may lower the resolution of the displays. The displays may also be scaled or have a data transform applied to them. For example, these operations could include taking a logarithm and/or applying a customized grayscale color map.

En-face angiogram projections may also be displayed at step 414 following filtering. The displays may include any of the filtered/smoothed (or unfiltered and unsmoothed) results from the previously described processing. The display visualizations may include vasculature within different zones of retinal tissue (in an inner/outer sense) such as the superficial retinal arteries and veins, peripapillary radial network, and the superficial capillary plexus; the deep capillary plexus; the choriocapillaris, the outer retina; and other disease- or pathology-specific views as appropriate. Furthermore, multiple projections may be displayed simultaneously, and any such images may also be presented simultaneously with the high-resolution OCT or angiography cross-section images, or with the corresponding OCT structural en-face images. Any combinations of the various image permutations are possible within the scope of the present disclosure. The projections may be calculated by taking the maximum intensity projection (MIP) in each A-line. In other embodiments, the projection may be calculated by taking the mean, median, or an arbitrary quantile. The projections may also be calculated by taking the mean of all values above a certain threshold. This threshold may be customizable by the user of the system.

According to the fifth aspect, no windowing functions or those with low equivalent noise bandwidth (ENBW) characteristics, and/or spectral reshaping may be utilized. As used herein, the ENBW of a window is the width of a rectangle filter with the same peak power gain that would accumulate the same noise power. Assuming a sampling interval T=1, for a generalized complex window function w(nT), the ENBW is given according to:

$$ENBW = \frac{\sum_n |w(n)|^2}{|\sum_n w(n)|^2}$$

In some OCT signal processing methods, windowing functions or reshaping of the interferogram data are used to abate discontinuities in the spectral data and to shape the signal waveform, such that when viewed as a periodic signal, is roughly smooth and continuous (e.g., no excessively high frequencies). This is because such discontinuities and high frequencies may result in spectral leakage from a discrete Fourier transform (DFT). For example, a Hann or equivalent windowing function (to achieve a Gaussian or similar waveform) may be used. However, rectangular windowing functions can yield superior angiographic projection results, for example, with respect to finer vessel structures typical in the retina. These finer vessels can appear to be better connected in projection images, resulting in an angiographic projection that appears to be more realistic and have a higher resolution.

Despite these advantages, by not applying a window or applying a rectangular window, then some degree of streaking may appear in the OCT images. This may lead to a system design tradeoff in which angiographic results improve at the expense of the clean appearance of the component OCT images. Thus, OCT structural images can be processed using one window function (e.g., a Hann window) while angiographic images can be processed using another window function (e.g., a rectangular window or window with a lower ENBW). Further, operations such as registration at step 404 and/or segmentation at step 408 may be based on one or the other of the sets of images. For example, it may be advantageous for segmentation, even if applied to the angiographic images, to have been computed based on a Hann windowing function due to sharper image edges associated with less signal leakage. Similarly, in the case of inter-image registrations, it may be beneficial to register only the sharper set of OCT component images to be utilized with respect to the OCT structural images. Then the determined transform parameters can be reused for angiographic purposes with respect to the blurrier component frames.

Figure 7:
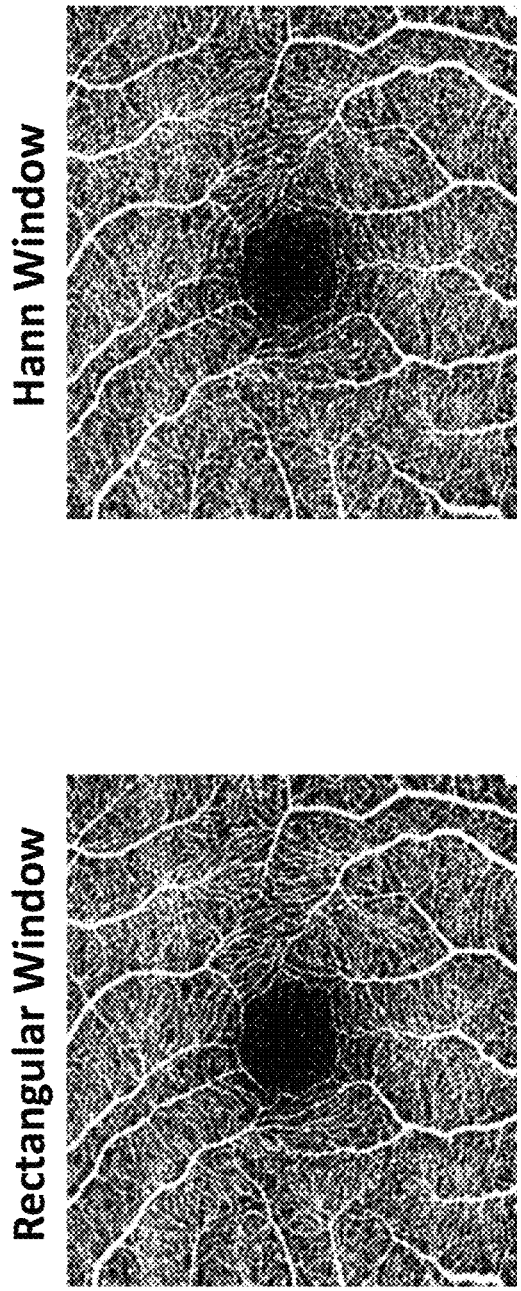
FIG. 7 illustrates a comparison of the results of a rectangular window and a Hann window.

The transfer functions of typical window functions, such as the Hann window, have values on the order of about, for example, 50-100 dB down (and often more) away from the center lobe. On the other hand, rectangular windows typically have a transfer function with values on the order of about, for example, 20 dB. While the use of a window function (or a similarly designed spectral reshaping function) with a lower ENBW may have the effect of inducing signal leakage, which may effectively cause blurring, it may also effectively reduce the calculation effects associated with deconstructive speckle. This is because such pixels, which might otherwise have very low intensity values and, therefore, might be more likely to result in more extreme ratio results when paired with corresponding pixels in other frames, will be effectively increased in intensity by a degree that is greater than for other pixels of higher intensity. This effectively serves to apply a floor to signal intensities in the OCT images and, in turn, may moderate computed ratio values. As a result, the angiographic calculations may be more stable and reliable, and the angiographic image may have an improved signal-to-noise ratio. A comparison of the results of an example swept source based angiogram utilizing a rectangular window and a Hann window are illustrated in FIG. 7. As can be seen, the processing with the rectangular window leads to reduced noise (e.g. in and surrounding the foveal avascular zone), apparently higher angiographic signal-to-noise ratio/fidelity, and better overall connectedness of the inner retinal (superficial) vasculature.

While the rectangular window was described in the above examples, it is noted that other window functions, including those not traditionally thought of as high-resolution OCT windows, may be used. For example, a Tukey window with a low alpha (such as 0.1 or less) may be used. Tukey windows have a relative advantage when compared to rectangular windows in that a possible discontinuity in the spectrum is abated and, therefore, effects to the OCT images themselves (e.g., streaking) may be reduced. Still, windowing functions that have an ENBW that is notably less than that of the Hann window can be expected to perform in substantially the same manner as the rectangular window. For example, an ENBW less than about 1.23 can yield superior angiographic projection results. It is also noted that the spectrum may be shaped by either or both optical and/or numerical methods, and the lower ENBW characteristic discussed above may be applied thereto.

While the above description relates to particular windowing functions, these functions are not intended to limit the scope of the present disclosure. Still further, the windowing functions may be implemented as either hardware or software, and the ENBW criteria can be applied. For example, criteria such as the ENBW may be applied to the envelope of the interferogram as it is immediately before a discrete Fourier transform. However, the present disclosure should not be limited to this timing.

With respect to the sixth aspect described herein, OCT images for angiography may be computed using a partial spectrum that represents a subset of the full spectral data. This may be desirable in some scenarios, such as when spectral reshaping is utilized. This may yield improved results as spectral reshaping may effectively amplify the signal-to-noise ratio over some portions of the spectrum.

With respect to a seventh aspect described herein, a minimum intensity threshold can be applied within the general calculation methodology to determine over which pixels to calculate a ratio-based or geometric standard deviation result. According to this aspect, when the signal intensity of a particular pixel location is at or above the minimum intensity, the value (e.g. ratio value) is calculated. Otherwise, the angiographic output is set to zero (or any arbitrary value).

The minimum intensity threshold can be calculated relative to weak foreground signal (e.g., relatively hyporeflective retinal signal in the case of retinal angiography). In contrast to a minimum intensity threshold based on calculations relative to a measured background noise (e.g., when a sample beam is blocked from detection or in portions of an image that do not correspond to any sample or that have scattering properties to which the system lacks sensitivity), the threshold based on a weak foreground signal can yield a better signal-to-noise ratio in the resulting angiographic image and greater continuity of the imaged vasculature. The foreground-based threshold also allows a consistently high quality result to be delivered via a default parameter set. In other words, consistent angiography results can be achieved across various machines with differing noise characteristics.

Nevertheless, the background-based threshold may still be used without departing from the scope of the present disclosure.

Figure 8:
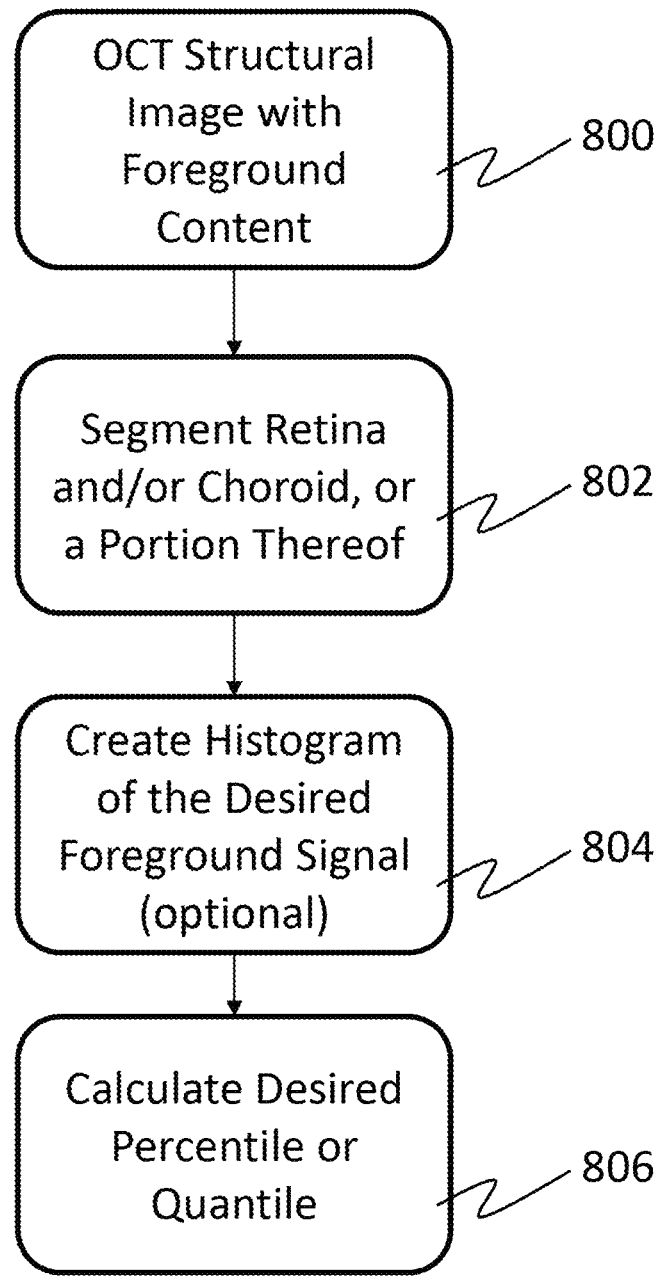
FIG. 8 is a flowchart for determining a minimum intensity threshold.

FIG. 8 illustrates a flow chart for determining the minimum intensity threshold using a weak foreground signal. According to one embodiment, an OCT image obtained at step 800, which can include ocular tissue, may be segmented at step 802 in any manner. For example, accurate layer boundaries may be determined in order to delineate the retina, choroid, and/or any desired layer. Alternatively, a moving window function of fixed or variable size may be used within each A-line to determine the foreground region by maximizing integrated signal content. Furthermore, the image(s) may be the same as that (those) being used to generate angiographic results, or they can be an entirely different image or set of images. This process could also be performed beforehand based on a representative image or set of images with the results stored as a calibration parameter or parameters.

Next, a histogram based on the segmented foreground data is optionally generated at step 804. This foreground data may correspond to the full retina and/or choroid. Alternatively, the foreground data may specifically correspond to a relatively hyporeflective layer or set of layers that might include the ganglion cell layer (GCL), inner nuclear layer (INL), or the outer nuclear layer (ONL). Then, using either the histogram or a sorted list of pixel intensities, a value is extracted at step 806 according to a predetermined percentile or quantile. For example, the full retina (which may include some choroid) is utilized to find the pixel intensity that falls at approximately the 25-30% percentile (a relatively low threshold) when ordered from low to high. If a hyporeflective layer or group of layers were utilized in the prior step, then a higher percentile could be used (e.g., between 50% (median) and 75%) with data ordered low to high. It is noted that any percentile level or pixel intensity may be used within the scope of the present disclosure based on desired results. The pixel intensity value at this point then serves as the minimum intensity threshold. The minimum intensity threshold can be automatically determined based on a fixed parameter (e.g., a prespecified percentile or quantile). In some embodiments, the parameter can be user-definable.

It is noted that the minimum intensity threshold may be based on the pixel intensity in any arbitrary image, including any of the individual frames or the averaged image. Additionally, different frame combinations could utilize a different image or images as the basis for determining a threshold.

Figure 9A:
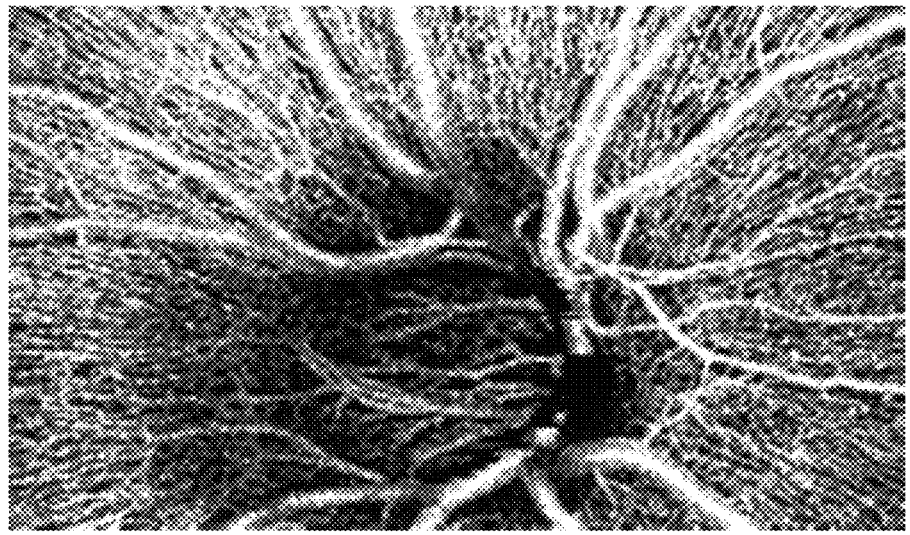
FIG. 9A illustrates comparative angiography images for a SSADA-like technique and techniques described herein.
Figure 9A:
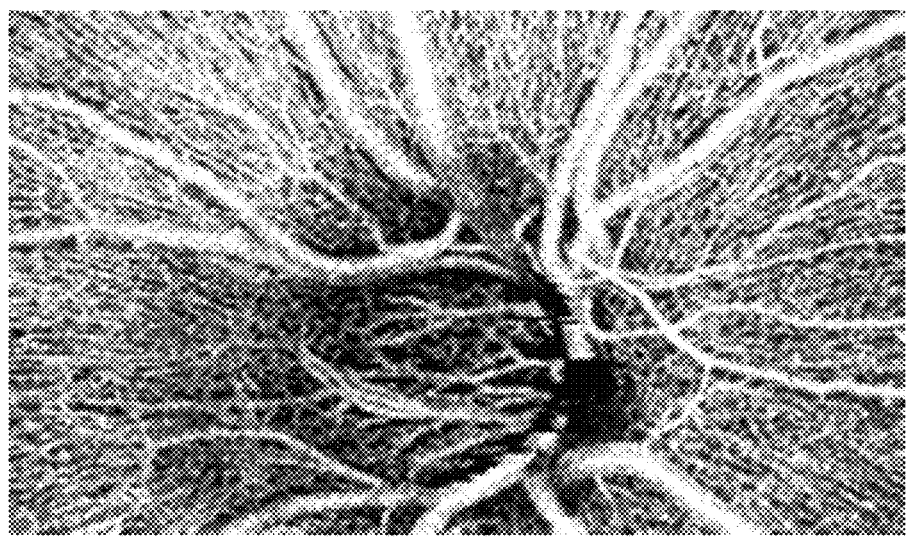
Figure 9B:
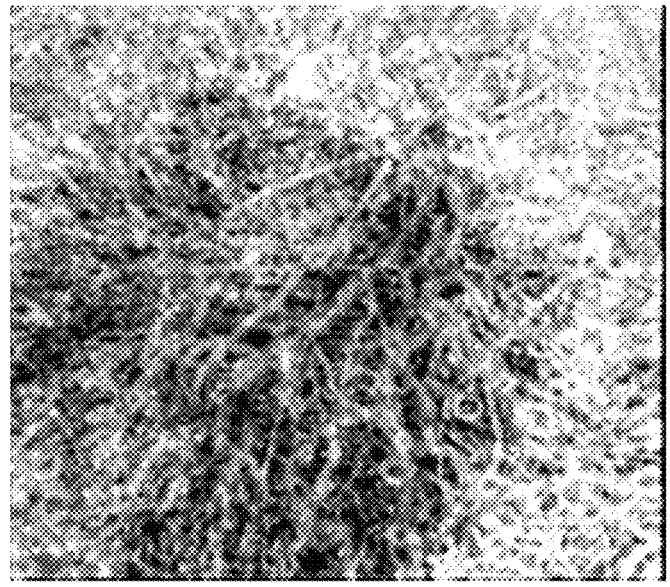
FIG. 9B illustrates comparative angiography images for standard deviation interframe calculations and techniques described herein.
Figure 9B:
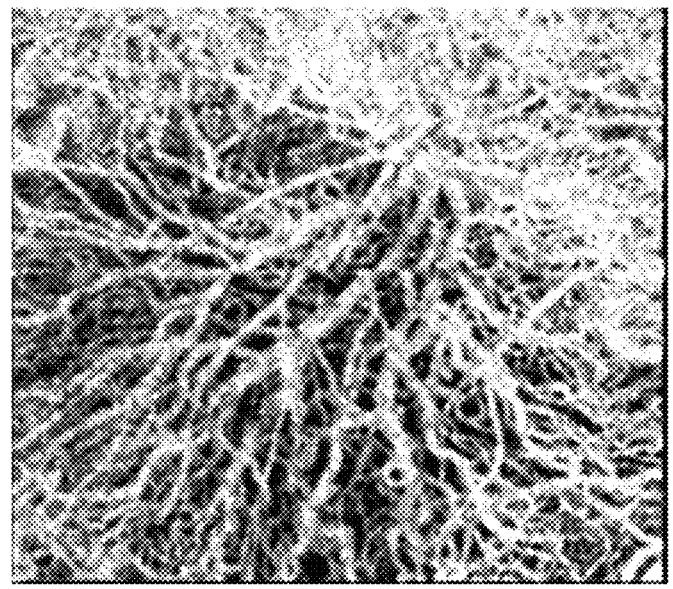

FIG. 9A illustrates a comparison between the SSADA method and a technique described herein. In FIG. 9, the same data set is calculated using a technique described herein and a method approximating SSADA processing. Both images are based on maximum intensity projection over identical depths and utilize the same normalization methodology in their displays. It can be seen that the image generated by the above-described technique provides greater angiographic signal intensity and detail, for example in and around the optic nerve head, resulting in an image with more consistent appearance. Similarly, FIG. 9B illustrates a comparison of choroidal neovascular membrane images between standard deviation interframe calculations and techniques described herein. Again, the image generated by the above-described technique provides greater angiographic signal intensity and detail, as well as greater consistency across the imaging area.

Figure 10:
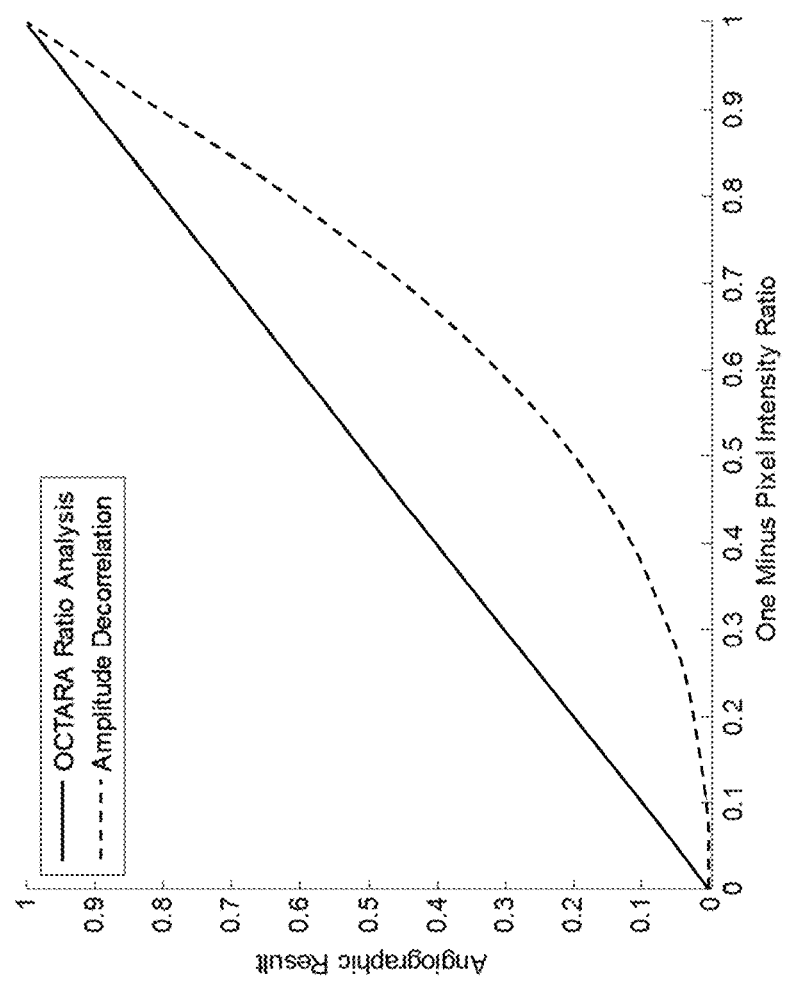
FIG. 10 is a plot that graphically demonstrates the relative sensitivity advantage of a ratio-based approach over amplitude decorrelation.

FIG. 10 further illustrates a comparison between amplitude decorrelation methods and those described herein by plotting the relative sensitivity advantage of a ratio-based approach over amplitude decorrelation. As can be seen, for lower flows (those having a low one minus pixel intensity ratio), ratio-based method (OCTARA Ratio Analysis) provides a greater angiographic result. Accordingly, images formed through a ratio-based analysis are more sensitive (clearer distinction) to vasculature with lower blood flows. For example, based on the plot of FIG. 10, the ratio-based method is about as sensitive to a 0.1 on minus pixel intensity ratio, as amplitude decorrelation is for a 0.4 one minus pixel intensity ratio. Furthermore, similar to the tabular data presented above, given the curvature of the two plot lines it can be observed that the ratio-based analysis demonstrates greater sensitivity to lower blood flows relative to the flow at greater, intermediate levels as well. The ratio-based result, therefore, is associated with both greater linearity as well as higher dynamic range.

It is also noted that parameters of the OCT system used for imaging can have an effect on the resultant images. That is, for example, OCT angiography can require repeated scanning of the same position in the eye and, therefore, higher OCT imaging rates can benefit OCT angiography to acquire densely sampled data sets. However, OCT imaging sensitivity scales inversely with speed and is limited by the maximum permissible exposure (MPE) values of standards such as ANSI Z136.1, ISO 15004-2 or IEC 60825-1. The maximum achievable sensitivity of a high speed (Fourier-domain) OCT in the case of a perfect reflector and lossless optical system is given as:

$$\text{Sensitivity} = 10 \log_{10}\left(\frac{\rho P_{MPE}}{2ef_A}\right)$$

where $\rho$ is the photodetector responsivity, $P_{MPE}$ is the MPE optical power on the eye, e is the charge of an electron, and $f_A$ the OCT imaging speed.

One feature of OCT angiography is its ability to detect blood flow in different layers of the retina. Both the motion contrast calculations and retinal layer segmentation rely on sufficient sensitivity in OCT imaging to enable enface visualization of each layer of vascular networks in the retina and choroid. With lower sensitivity, the higher noise not only detrimentally affects motion contrast calculations, but also can make it difficult to perform segmentation for visualizing vasculature within specific layers of the retina. Therefore, many clinical OCT devices require sensitivity above 95 dB. With a 1mm diameter beam incident on the cornea, the MPE is limited to 0.79 mW according to ISO 15004-2. Assuming a typical photodetector responsivity of 0.7 A/W, the maximum OCT imaging speed is less than 485 kHz to maintain a reasonable sensitivity according to the expression above.

A higher MPE can be allowed with a larger diameter beam incident on the cornea. However, a larger beam can decrease the robustness of the device by having smaller margins for misalignment through the pupil and shorter axial field of view at the beam focus. Even with an increased MPE, maximum OCT imaging speed suitable for clinical imaging is likely below 1 MHz given current safety standards. Averaging multiple OCT images can enhance image quality in high speed OCT, but it does not necessarily help OCT angiography motion contrast calculations. In light of the above, the OCT imaging speed for OCT angiography may be an A-scan rate of less than 1 MHz, for example several hundreds of kHz. For example, some OCT implementations may have an A-scan rate of 25 kHz-800 kHz. There are no such lower "boundaries" or "limits" other than considerations such as those relating to artifacts/noise from eye motion of the subject and desired scan density. Nevertheless, the aspects described herein may be used with any OCT system, or applied to data obtained with other imaging modalities.

While this disclosure is based on the OCT imaging modality, it is not limited to OCT. For example, it is applicable to ultrasound as well. It should also be noted that while a technique described herein is related to angiography and retinal vessel visualization, the techniques are not limited in this manner either; but rather, may be applied to other visualizations involving fluid or object flow, or other moving volumes. Flow or motion in the vitreous is one example.

It is to be noted that any of the aspects or combination of aspects described above may be implemented via hardware or software. When software, the computer program including instructions for causing a computer to execute at least a portion of the above-described aspects is stored on a non-transitory computer-readable medium. When executed the software causes a computer, including for example a processor(s), to execute the instructions stored thereon. These aspects may be implemented on a processor or a plurality of processors, such as a graphics processing unit (GPU) or similar dedicated graphics processor. These processor(s) also may be embedded or integrated with other processors designed for a separate purpose, for example, as part of a central processing unit (CPU). Such processor(s) may also be for general-purpose computing on a graphics processor unit (GPGPU). A "processor" as used herein refers to any, or part of any, electrical circuit comprised of any number of electrical components, including, for example, resistors, transistors, capacitors, inductors, and the like. The circuit may be of any form, including, for example, an integrated circuit, a set of integrated circuits, a microcontroller, a microprocessor, a collection of discrete electronic components on a printed circuit board (PCB) or the like. The processor may also stand alone or be part of a computer used for operations other than processing image data. Implementation of these aspects by hardware or software may be realized in any number of electronic devices and/or applications, including but not limited to, personal computers, servers, integrated OCT or similar imaging machines, and the like. Moreover, the above aspects and/or combination of aspects may be stored in memory which is executable by one of said processors. It should also be noted that the above description is non-limiting, and the examples are but only a few of many possible processors and implementations envisioned.

While various features are presented above, it should be understood that the features may be used singly or in any combination thereof. Further, it should be understood that variations and modifications may occur to those skilled in the art to which the claimed examples pertain. The examples described herein are exemplary. The disclosure may enable those skilled in the art to make and use alternative designs having alternative elements that likewise correspond to the elements recited in the claims. The intended scope may thus include other examples that do not differ or that insubstantially differ from the literal language of the claims. The scope of the disclosure is accordingly defined as set forth in the appended claims.

What is claimed is:

1. An angiographic optical coherence tomography (OCT) method comprising:
    calculating values of OCT images of a volume, the OCT images being B-scan frames repeatedly captured from a same location of the volume;
    generating an angiographic image based on the calculated values; and
    displaying, rendering, and/or storing the angiographic image, wherein the values are calculated by comparing respective pixels of a permutation of interframe combinations of the OCT images,
    wherein the permutation of interframe combinations comprises:
        a first interframe combination having frames separated by a first number of frames, and
        a second interframe combination having frames separated by a second number of frames, the second number of frames being different than the first number of frames.

2. The method of claim 1, wherein a contrast of each pixel of the angiographic image corresponds to a different one of the calculated values.

3. The method of claim 1, wherein:
    the calculated values represent a dissimilarity between the corresponding pixels, and
    a sensitivity of the calculated values to the dissimilarity is greater than a sensitivity of values determined according to an amplitude decorrelation method.

4. The method of claim 1, further comprising:
    averaging the calculated values for an X-Y position of the OCT images for which the values are calculated.

5. The method of claim 4, further comprising:
    comparing the averaged value to a criterion; and
    excluding the averaged value when the averaged value does not meet the criterion.

6. The method of claim 5, wherein the averaging, comparing, and excluding are performed A-line by A-line.

7. The method of claim 1, wherein at least one of the OCT images is captured by illumination with a partial spectrum of an OCT light source.

8. The method of claim 1, wherein the values are only calculated for corresponding pixels of the OCT images having an intensity greater than a minimum pixel intensity threshold.

9. The method of claim 8, wherein the minimum pixel intensity threshold is a pixel intensity at a predetermined percentile of pixel intensities according to a histogram or sorted list of pixels of at least a portion of the OCT images.

10. The method of claim 1, wherein A-scans of the OCT images are captured at a rate less than 1 MHz.

11. The method of claim 1, wherein A-scans of the OCT images are captured at a rate between 25 kHz and 800 kHz.

12. The method of claim 1, wherein the permutation of interframe combinations of the OCT images is predetermined.

13. The method of claim 1, wherein the permutation of interframe combinations of the OCT images comprises at least one combination of OCT images separated by more than one frame.

14. The method of claim 1, wherein the permutation of interframe combinations of the OCT images comprises at least two combinations of OCT images having different time separations.

15. An angiographic optical coherence tomography (OCT) method, comprising:
- calculating values of OCT images of a volume, the OCT images being B-scan frames repeatedly captured from a same location of the volume;
- generating an angiographic image based on the calculated values; and
- displaying, rendering, and/or storing the angiographic image,
- wherein the values are calculated by comparing respective pixels of a permutation of interframe combinations of the OCT images, and
- wherein an equivalent noise bandwidth (ENBW) for the OCT images is greater than the ENBW for the angiographic image.

16. An angiographic optical coherence tomography (OCT) method comprising:
- calculating values of a first OCT image, a second OCT image, and a third OCT image, the first, second, and third OCT images being B-scan frames repeatedly captured from a same location;
- generating an angiographic image based on the calculated values; and
- displaying, rendering, and/or storing the angiographic image,
- wherein the values are calculated by comparing respective pixels of the first and second OCT images, comparing respective pixels of the second and third OCT images, and comparing respective pixels of the first and third OCT images, and
- wherein the second OCT image is captured after the first OCT image, and the third OCT image is captured after the second OCT image.

* * * * *